(12) United States Patent
Ghosh et al.

(10) Patent No.: US 10,799,703 B2
(45) Date of Patent: Oct. 13, 2020

(54) EVALUATION OF HIS BUNDLE PACING THERAPY

(71) Applicant: Medtronic, Inc., Minneapolis, MN (US)

(72) Inventors: Subham Ghosh, Blaine, MN (US); Zhongping Yang, Woodbury, MN (US)

(73) Assignee: Medtronic, Inc., Minneapolis, MN (US)

( * ) Notice: Subject to any disclaimer, the term of this patent is extended or adjusted under 35 U.S.C. 154(b) by 224 days.

(21) Appl. No.: 15/853,102

(22) Filed: Dec. 22, 2017

(65) Prior Publication Data

US 2019/0192860 A1 Jun. 27, 2019

(51) Int. Cl.
| | |
|---|---|
| *A61N 1/37* | (2006.01) |
| *A61B 5/0408* | (2006.01) |
| *A61N 1/365* | (2006.01) |
| *A61B 5/04* | (2006.01) |
| *A61B 5/00* | (2006.01) |
| *A61N 1/05* | (2006.01) |
| *A61N 1/36* | (2006.01) |

(52) U.S. Cl.
CPC ........ *A61N 1/3706* (2013.01); *A61B 5/04012* (2013.01); *A61B 5/04085* (2013.01); *A61B 5/6823* (2013.01); *A61N 1/36507* (2013.01); *A61B 5/686* (2013.01); *A61N 1/36114* (2013.01); *A61N 2001/0585* (2013.01)

(58) Field of Classification Search
CPC .............. A61N 1/3706; A61N 1/36507; A61N 1/36114; A61N 2001/0585; A61B 5/6823; A61B 5/04012; A61B 5/04085; A61B 5/686

See application file for complete search history.

(56) References Cited

U.S. PATENT DOCUMENTS

| | | |
|---|---|---|
| 4,233,987 A | 11/1980 | Feingold |
| 4,402,323 A | 9/1983 | White |
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |

(Continued)

FOREIGN PATENT DOCUMENTS

| | | |
|---|---|---|
| CN | 1043621 A | 7/1990 |
| CN | 1253761 A | 5/2000 |

(Continued)

OTHER PUBLICATIONS

International Search Report and Written Opinion dated May 3, 2012 for International Application No. PCT/US2012/036262; 9 pages.

(Continued)

*Primary Examiner* — Mark Bockelman
(74) *Attorney, Agent, or Firm* — Mueting Raasch Group

(57) ABSTRACT

Cardiac electrical heterogeneity information may be used to determine whether one or more His bundle paced settings for His bundle pacing therapy are acceptable for His bundle pacing. Cardiac electrical heterogeneity information may be generated during His bundle pacing, and the evaluation against baseline information and/or other information to determine whether the His bundle paced settings are acceptable.

16 Claims, 11 Drawing Sheets

(56) References Cited

U.S. PATENT DOCUMENTS

| | | |
|---|---|---|
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,937,897 B2 | 8/2005 | Min et al. |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,027,876 B2 | 4/2006 | Casavant et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Miassig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harley et al. |
| 7,953,482 B2 | 5/2011 | Hess |
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B2 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |

(56) References Cited

U.S. PATENT DOCUMENTS

| | | |
|---|---|---|
| 9,320,446 B2 | 4/2016 | Gillberg et al. |
| 9,474,457 B2 | 10/2016 | Ghosh et al. |
| 9,486,151 B2 | 11/2016 | Ghosh et al. |
| 9,510,763 B2 | 12/2016 | Gosh et al. |
| 9,586,050 B2 | 3/2017 | Ghosh et al. |
| 9,586,052 B2 | 3/2017 | Gillberg et al. |
| 9,591,982 B2 | 3/2017 | Ghosh et al. |
| 9,610,045 B2 | 4/2017 | Du et al. |
| 9,764,143 B2 | 9/2017 | Ghosh et al. |
| 9,776,009 B2 | 10/2017 | Ghosh et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min et al. |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1 | 5/2014 | Ramanathan et al. |

(56) References Cited

U.S. PATENT DOCUMENTS

| | | | |
|---|---|---|---|
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Ghosh |
| 2016/0331258 A1 | 11/2016 | Du et al. |
| 2017/0027463 A1 | 2/2017 | Du et al. |

FOREIGN PATENT DOCUMENTS

| | | | |
|---|---|---|---|
| CN | 1878595 A | 12/2006 |
| CN | 101073502 A | 11/2007 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

International Search Report and Written Opinion dated May 3, 2012 for International Application No. PCT/US2012/036302; 9 pages.
International Search Report and Written Opinion dated Aug. 6, 2014 for International Application No. PCT/US2014/036153; 14 pages.
International Search Report and Written Opinion dated Nov. 7, 2014 for International Application No. PCT/US2014/036163; 12 pages.
International Search Report and Written Opinion dated Oct. 28, 2014 for International Application No. PCT/US2014/041928; 15 pages.
International Search Report and Written Opinion dated Oct. 24, 2014 for International Application No. PCT/US2014/041929; 14 pages.
International Search Report and Written Opinion dated Nov. 4, 2014 for International Application no. PCT/US2014/0247583; 7 pages.
International Search Report and Written Opinion dated Nov. 12, 2014 for International Application No. PCT/US2014/047971; 7 pages.
International Search Report and Written Opinion dated Nov. 12, 2014 for International Application No. PCT/US2014/048120; 7 pages.
International Search Report and Written Opinion dated Mar. 9, 2015 for International Application No. PCT/US2014/069214; 11 pages.
International Search Report and Written Opinion dated Mar. 17, 2015, for International Application No. PCT/US2014/069192; 11 pages.
International Search Report and Written Opinion dated Mar. 16, 2015 for International Application No. PCT/US2014/069182; 11 pages.
International Search Report and Written Opinion dated Apr. 8, 2015 for International Application No. PCT/US2014/069070; 11 pages.
International Search Report and Written Opinion dated Jun. 11, 2015 for International Application No. PCT/US2015/021442; 13 pages.
Biffi et al., "Occurrence of Phrenic Nerve Stimulation in Cardiac Resynchronization Therapy Patients: the Role of Left Ventricular Lead Type and Placement Site," *Europace*, 2013; 15:77-82.
Botker MD, PhD., et al., "Electromechanical Mapping for Detection of Myocardial Viability in Patients with ischemia Cardiomyopathy," Circulation, Mar. 2001; vol. 103, No. 12, pp.
"CardioGuide System Enables Real-Time Navigation of Left Ventricular Leads During Medtronic CRT Implants," Press Release, Apr. 9, 2013, Medtronic, Inc., 2 pgs.
Cuculich, P.S., et al., "The Electrophysiological Cardiac Ventricular Substrate in Patients After Myocardial Infection" J. Am. Coll. Cardiol. 2011; 58:1893-1902.
Czerwinska et al., "Method of Segmentation of Thorax Organs Images Applied to Modeling the Cardiac Electrical Field," *Engineering in Medicine and Biology Society*, Proceedings of the 22$^{nd}$ Annual International Conference of the IEEE, vol. 1, 23, Jul. 23, 2000.; pp. 402-405.
Dawoud, F. et al., "Inverse Electrocardiographic Imaging to Assess Electrical Dyssynchrony in Cardiac Resynchronization Therapy Patients," Computing in Cardiology, 2012; 39:993-996.

(56) References Cited

OTHER PUBLICATIONS

Freund et al., "A Decision-Theoretic Generalization of Online Learning and an Application to Boosting," *Journal of Computer and System Sciences*, 1997; 55(1):119-139.
Friedman, "Greedy Function Approximation: A Gradient Boosting Machine," *Annals of Statistics*, 2001; 29(5):1189-1232.
Friedman, "Stochastic Gradient Boosting," *Computational Statistics and Data Analysis*, 2002; 38(4):367-378.
Friedman et al.. "Additive Logistic Regression: a Statistical View of Boosting," *Annals of Statistics*, 2000; 28(2):337-374.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9):1469-1475.
"Heart Failure Management" datasheet [online]. Medtronic, Minneapolis, Minnesota, [Last updated on Jun. 3, 2013].Retrieved from the Internet: www.medtronic.com; 9 pages.
Hopenfeld et al., "The Effect of Conductivity on ST-Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Medtronic Vitatron Carelink Encore® Programmer Model 29901 Reference Manual, 2013, Medtronic, Inc., Minneapolis, MN.
Miri et al., "Applicability of body surface potential map in computerized optimization of biventricular pacing," Annals of Biomedical Engineering, vol. 38, No. 3, Mar. 2010, pp. 865-875.
Miri et al., "Comparison of the electrophysiologically based optimization methods with different pacing parameters in patient undergoing resynchronization treatment," 30th Annual International IEEE EMBS Conference, Aug. 2008, pp. 1741-1744.
Miri et al., "Computerized Optimization of Biventricular Pacing Using Body Surface Potential Map," 31st Annual International Conference of the IEEE EMBS, Sep. 2009, pp. 2815-2818.
Miri et al., "Efficiency of Timing Delays and Electrode Positions in Optimization of Biventricular Pacing: A Simulation Study," IEEE Transactions on Biomedical Engineering, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" *Circulation*, 2013; 128: 2407-2418.
Ridgeway, "The State of Boosting," *Computing Science and Statistics*, 1999; 31:172-181.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—a Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms: a simulation study," Circulation Research, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-34. Available online Jan. 25, 2010.
Sweeney et al., QRS Fusion Complex Analysis Using Wave Interference to Predict Reverse Remodeling During Cardiac Resynchronization Therapy, heart Rhythm, 2014, 11:806-813.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Easy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," Annals of Biomedical Engineering, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and no Dyssynchrony," *Circulation*, Oct. 27, 2009; 120: 1687-1694.

EVALUATION OF HIS BUNDLE PACING THERAPY

The disclosure herein relates to systems and methods for use in the evaluation of His bundle pacing therapy.

SUMMARY

The exemplary systems, methods, and interfaces described herein may be configured to assist a user (e.g., a physician) in evaluating a patient and/or evaluating cardiac therapy (e.g., cardiac therapy being performed on a patient during and/or after implantation of cardiac therapy apparatus). In one or more embodiments, the systems, methods, and interfaces may be described as being noninvasive. For example, in some embodiments, the systems, methods, and interfaces may not need, or include, implantable devices such as leads, probes, sensors, catheters, implantable electrodes, etc. to monitor, or acquire, a plurality of cardiac signals from tissue of the patient for use in evaluating the patient and/or cardiac therapy. Instead, the systems, methods, and interfaces may use electrical measurements taken noninvasively using, e.g., a plurality of external electrodes attached to the skin of a patient about the patient's torso.

In at least one embodiment, the exemplary systems and methods can include monitoring electrical activity of a patient to determine electrical heterogeneity information associated with the patient's cardiac activity. The electrical heterogeneity information can be used to determine whether a paced setting is acceptable for delivering His bundle pacing therapy. In response to the paced setting being unacceptable, additional monitoring and determinations of electrical heterogeneity information can be performed using a variety of paced settings in order to determine which of the paced settings are acceptable.

One exemplary system may include an electrode apparatus. The electrode apparatus can include a plurality of external electrodes to monitor electrical activity from tissue of a patient. The exemplary system can include a computing apparatus. The computing apparatus can include processing circuitry and can be coupled to the electrode apparatus. The computing apparatus can be configured to monitor electrical activity using the plurality of external electrodes. The computing apparatus can be further configured to generate His bundle electrical heterogeneity information based on the monitored electrical activity during delivery of His bundle pacing therapy at one or more His bundle paced settings. The His bundle electrical heterogeneity information can be representative of at least one of mechanical cardiac functionality and electrical cardiac functionality. The computing apparatus can be further configured to determine whether one or more of the His bundle paced settings for the His bundle pacing therapy are acceptable based on the electrical heterogeneity information.

In at least one embodiment, an exemplary method can include monitoring electrical activity from tissue of a patient using a plurality of external electrodes. The method can further include generating His bundle therapy electrical heterogeneity information based on the monitored electrical activity during delivery of His bundle pacing therapy at a one or more His bundle paced settings. The His bundle therapy electrical heterogeneity information can be representative of at least one of mechanical cardiac functionality and electrical cardiac functionality. The method can further include determining whether the one or more His bundle paced settings associated with the His bundle pacing therapy are acceptable based on the electrical heterogeneity information.

In at least one embodiment, an exemplary system can include an electrode apparatus. The electrode apparatus can include a plurality of external electrodes to monitor electrical activity from tissue of a patient. The exemplary system can include computing apparatus. The computing apparatus can include processing circuitry and can be coupled to the electrode apparatus. The computing apparatus can be configured to monitor electrical activity using the plurality of external electrodes during delivery of His bundle pacing therapy. The computing apparatus can be further configured to generate electrical heterogeneity information during delivery of His bundle pacing therapy. The computing apparatus can be further configured to determine whether a His bundle paced setting for the His bundle pacing therapy is acceptable based on the electrical heterogeneity information generated from the electrical activity using the His bundle paced setting. The computing apparatus can be further configured to adjust the paced setting for the His bundle pacing therapy based on whether the His bundle pacing therapy is acceptable.

The above summary is not intended to describe each embodiment or every implementation of the present disclosure. A more complete understanding will become apparent and appreciated by referring to the following detailed description and claims taken in conjunction with the accompanying drawings.

DETAILED DESCRIPTION OF EXEMPLARY EMBODIMENTS

Figure 1:
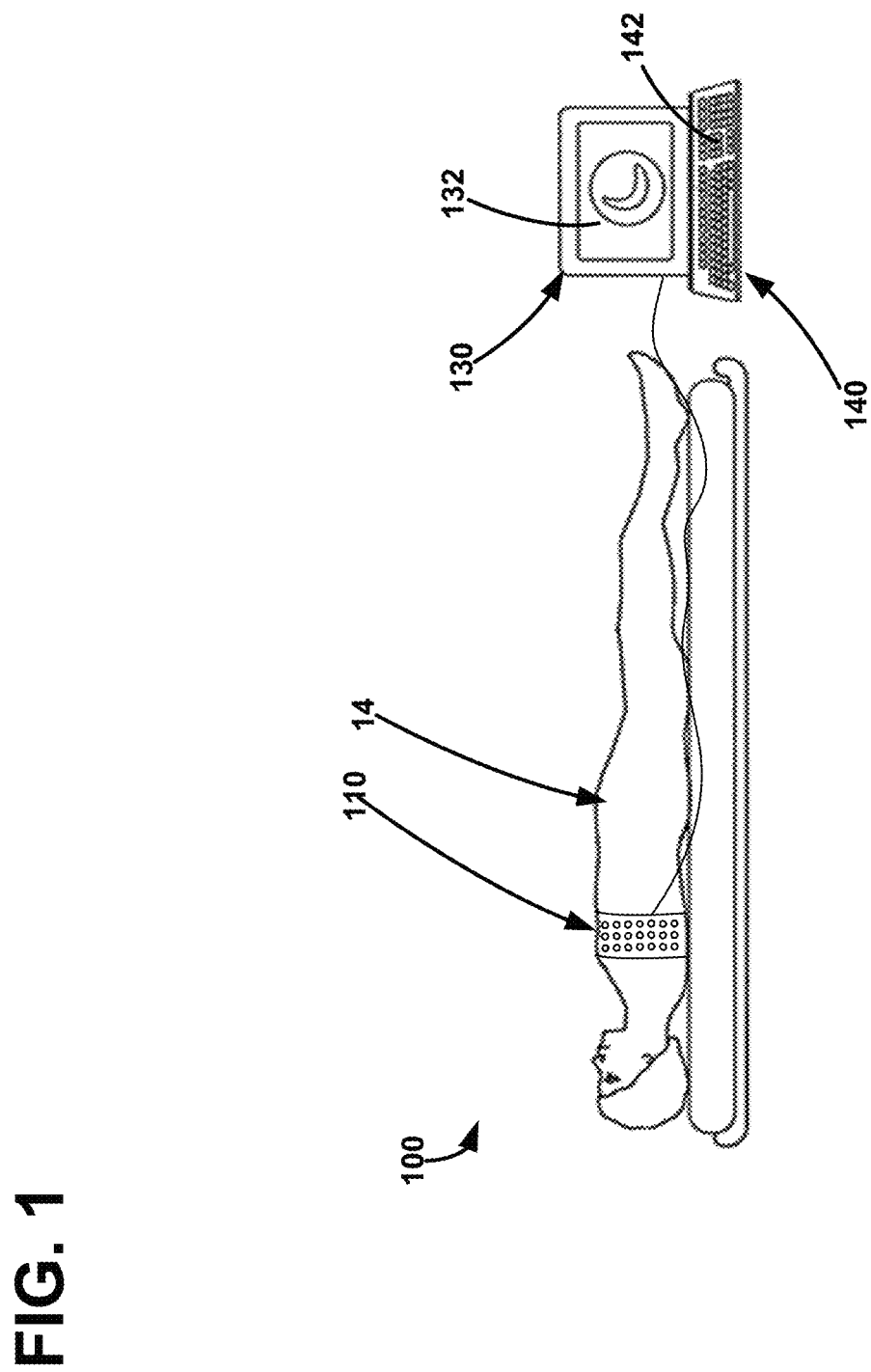
FIG. 1 is a diagram of an exemplary system including electrode apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

Exemplary systems and methods shall be described with reference to FIGS. 1-11. It will be apparent to one skilled in the art that elements or processes from one embodiment may be used in combination with elements or processes of the other embodiments, and that the possible embodiments of such methods and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

Cardiac electrical activation times can be detected or estimated in proximity of a reference location (e.g., which can be a chosen location for implantation of a lead for His bundle pacing cardiac therapy) using unipolar electrocardiogram (ECG) recordings. Such electrical activation times may be measured and displayed, or conveyed, to an implanter by a system which acquires the ECG signals and generates various metrics of electrical activation times (e.g., depolarization) measured from various ECG locations.

Various exemplary systems, methods, and interfaces described herein may be configured to use electrode apparatus including external electrodes, display apparatus, and computing apparatus to noninvasively assist a user (e.g., a physician) in the evaluation of a patient's condition and/or His bundle pacing cardiac therapy being performed on, or delivered to, a patient. The His bundle, or bundle of His, can refer to a collection of heart muscle cells specialized for electrical conduction. The His bundle can transmit electrical impulses from the atrial-ventricular (AV) node (located between the atria and ventricles) to a point of the apex of the fascicular branches via the bundle branches. The fascicular branches then lead to the Purkinje fibers, which can provide fast electrical conduction to the ventricles, thereby causing the cardiac muscle of the ventricles to contract more efficiently at a paced interval. Traditional cardiac pacing therapies have included electrical stimulation of ventricular muscle which provides an alternative pathway of electrical activation usually bypassing the fast conduction path provided by His bundle and Purkinje fibers, often resulting in slower cell to cell conduction and lower efficiency in cardiac contraction than that potentially achievable through successful stimulation of the His bundle. In some examples, optimization of His bundle pacing therapy can correct bundle branch block in heart failure in contrast to using biventricular pacing.

An exemplary system 100 including electrode apparatus 110, display apparatus 130, and computing apparatus 140 is depicted in FIG. 1. The electrode apparatus 110 as shown includes a plurality of electrodes incorporated, or included, within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis, evaluation, etc. Exemplary electrode apparatus may be described in U.S. Pat. No. 9,320,446 entitled "Bioelectric Sensor Device and Methods" and issued on Apr. 26, 2016, which is incorporated herein by reference in its entirety. Further, exemplary electrode apparatus 110 will be described in more detail in reference to FIGS. 2-3.

Although not described herein, the exemplary system 100 may further include imaging apparatus. The imaging apparatus may be any type of imaging apparatus configured to image, or provide images of, at least a portion of the patient in a noninvasive manner. For example, the imaging apparatus may not use any components or parts that may be located within the patient to provide images of the patient except noninvasive tools such as contrast solution. It is to be understood that the exemplary systems, methods, and interfaces described herein may further use imaging apparatus to provide noninvasive assistance to a user (e.g., a physician) to locate or select a pacing electrode or pacing vector proximate the patient's heart for His bundle pacing therapy in conjunction with the evaluation of His bundle pacing therapy.

For example, the exemplary systems, methods, and interfaces may provide image guided navigation that may be used to navigate leads including electrodes, leadless electrodes, wireless electrodes, catheters, etc., within the patient's body while also providing noninvasive cardiac therapy evaluation including determining whether a His bundle paced setting is acceptable or determining whether one or more selected parameters are acceptable, such as selected location information (e.g., location information for the electrodes to target the His bundle). Exemplary systems and methods that use imaging apparatus and/or electrode apparatus may be described in U.S. Patent Publication No. 2014/0371832 filed on Jun. 12, 2013 and entitled "Implantable Electrode Location Selection," U.S. Patent Publication No. 2014/0371833 filed on Jun. 12, 2013 and entitled "Implantable Electrode Location Selection," U.S. Patent Publication No. 2014/0323892 filed on Mar. 27, 2014 and entitled "Systems, Methods, and Interfaces for Identifying Effective Electrodes," U.S. Patent Publication No. 2014/0323882 filed on Mar. 27, 2014 and entitled "Systems, Methods, and Interfaces for Identifying Optical Electrical Vectors," each of which is incorporated herein by reference in its entirety. Further exemplary His bundle pacing may be described in U.S. Pat. No. 6,937,897 issued on Aug. 30, 2005 and entitled "Electrode for His bundle stimulation," and U.S. Pat. No. 7,027,876 issued on Apr. 11, 2006 and entitled "Lead system for providing electrical stimulation to the Bundle of His," each of which is incorporated herein by reference in its entirety.

Exemplary imaging apparatus may be configured to capture x-ray images and/or any other alternative imaging modality. For example, the imaging apparatus may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative Mill, etc. Further, it is to be understood that the imaging apparatus may be configured to capture a plurality of consecutive images (e.g., continuously) to provide video frame data. In other words, a plurality of images taken over time using the imaging apparatus may provide video frame, or motion picture, data. Additionally, the images may also be obtained and displayed in two, three, or four dimensions. In more advanced forms, four-dimensional surface rendering of the heart or other regions of the body may also be achieved by incorporating heart data or other soft tissue data from a map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data, e.g., to be used to navigate treatment apparatus proximate target locations (e.g., such as within the His bundle) within the heart or other areas of interest.

Systems and/or imaging apparatus that may be used in conjunction with the exemplary systems and method described herein are described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which is incorporated herein by reference in its entirety.

The display apparatus 130 and the computing apparatus 140 may be configured to display and analyze data such as, e.g., electrical signals (e.g., electrocardiogram data), cardiac information representative of at least one of mechanical cardiac functionality and electrical cardiac functionality, etc. Cardiac information may include, e.g., electrical heterogeneity information or electrical dyssynchrony information, surrogate electrical activation information or data, etc. that is generated using electrical signals gathered, monitored, or collected, using the electrode apparatus 110. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in evaluating a pacing location (e.g., the location of an implantable electrode used for pacing, the location of pacing therapy delivered by a particular pacing vector, etc.).

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 and to view and/or select one or more pieces of information related to the cardiac therapy.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including cardiac information, textual instructions, graphical depictions of electrical activation information, graphical depictions of anatomy of a human heart, images or graphical depictions of the patient's heart, graphical depictions of locations of one or more electrodes, graphical depictions of a human torso, images or graphical depictions of the patient's torso, graphical depictions or actual images of implanted electrodes and/or leads, etc. Further, the display apparatus 130 may include a liquid crystal display, an organic light-emitting diode screen, a touchscreen, a cathode ray tube display, etc.

The processing programs or routines stored and/or executed by the computing apparatus 140 may include programs or routines for computational mathematics, matrix mathematics, dispersion determinations (e.g. standard deviations, variances, ranges, interquartile ranges, mean absolute differences, average absolute deviations, etc.), filtering algorithms, maximum value determinations, minimum value determinations, threshold determinations, moving windowing algorithms, decomposition algorithms, compression algorithms (e.g., data compression algorithms), calibration algorithms, image construction algorithms, signal processing algorithms (e.g., various filtering algorithms, Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, electrical signal/waveform data from the electrode apparatus 110, dispersions signals, windowed dispersions signals, parts or portions of various signals, electrical activation times from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein (e.g., electrical signals, cardiac information, etc.), or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information.

The output information may be applied as input to one or more other devices and/or methods as described herein or as would be applied in a known fashion.

The one or more programs used to implement the systems, methods, and/or interfaces described herein may be provided using any programmable language, e.g., a high-level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.) and may be generally described as including processing circuitry. The exact configuration of the computing apparatus 140 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable medium such as a disk or tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

Figure 2:
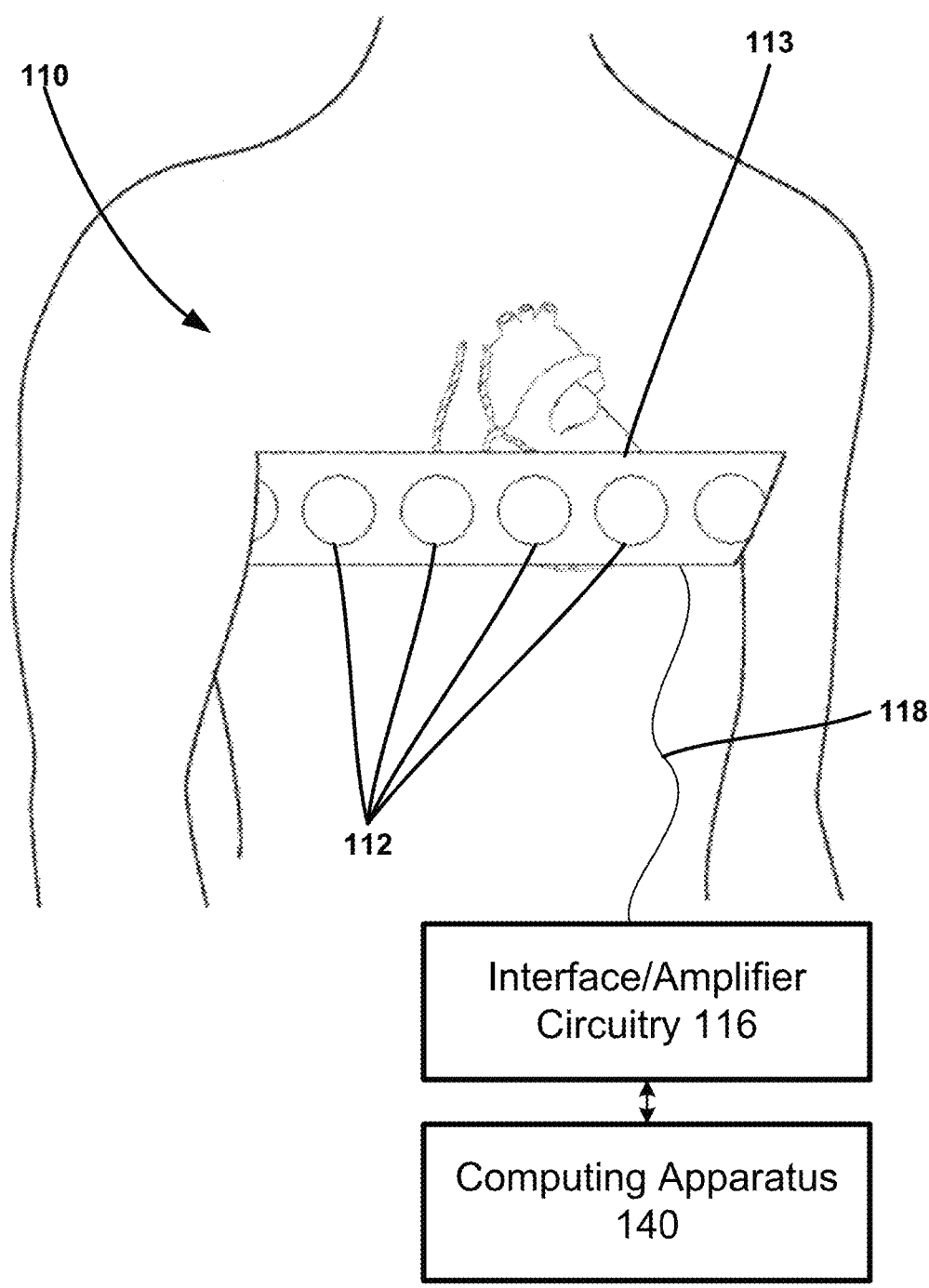
FIGS. 2-3 are diagrams of exemplary external electrode apparatus for measuring torso-surface potentials.

Electrical activation times of the patient's heart may be useful to evaluate a patient's cardiac condition and/or His bundle cardiac therapy being delivered to a patient. Surrogate electrical activation information or data of one or more regions of a patient's heart may be monitored, or determined, using electrode apparatus 110 as shown in FIG. 1 and in FIG. 2-3. The exemplary electrode apparatus 110 may be configured to measure body-surface potentials of a patient 14 and, more particularly, torso-surface potentials of a patient 14. As shown in FIG. 2, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of a patient 14 such that the electrodes 112 surround the patient's heart. As further illustrated, the electrodes 112 may be positioned around the circumference of a patient 14, including the posterior, lateral, posterolateral, anterolateral, and anterior locations of the torso of a patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data. For example, the interface/amplifier circuitry 116 may be electrically coupled to each of the computing apparatus 140 and the display apparatus 130 using, e.g., analog electrical connections, digital electrical connections, wireless connections, bus-based connections, network-based connections, internet-based connections, etc.

Although in the example of FIG. 2 the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other manners of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of a patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the electrical activity (e.g., torso-surface potential signals) sensed by electrodes 112 and amplified/conditioned by the interface/amplifier circuitry 116. The computing apparatus 140 may be configured to analyze the signals from the electrodes 112 to provide as anterior and posterior electrode signals and surrogate cardiac electrical activation times, e.g., representative of actual, or local, electrical activation times of one or more regions of the patient's heart as will be further described herein. Further, the electrical signals measured at the left anterior surface location of a patient's torso may be representative, or surrogates, of electrical signals of the left anterior left ventricle region of the patient's heart, electrical signals measured at the left lateral surface location of a patient's torso may be representative, or surrogates, of electrical signals of the left lateral left ventricle region of the patient's heart, electrical signals measured at the left posterolateral surface location of a patient's torso may be representative, or surrogates, of electrical signals of the posterolateral left ventricle region of the patient's heart, and electrical signals measured at the posterior surface location of a patient's torso may be representative, or surrogates, of electrical signals of the posterior left ventricle region of the patient's heart. In one or more embodiments, measurement of activation times can be performed by measuring the period of time between an onset of cardiac depolarization (e.g., onset of QRS complex) and an appropriate fiducial point such as, e.g., a peak value, a minimum value, a minimum slope, a maximum slope, a zero crossing, a threshold crossing, etc.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to evaluate a patient's cardiac condition and/or His bundle pacing therapy being delivered to the patient.

Figure 3:
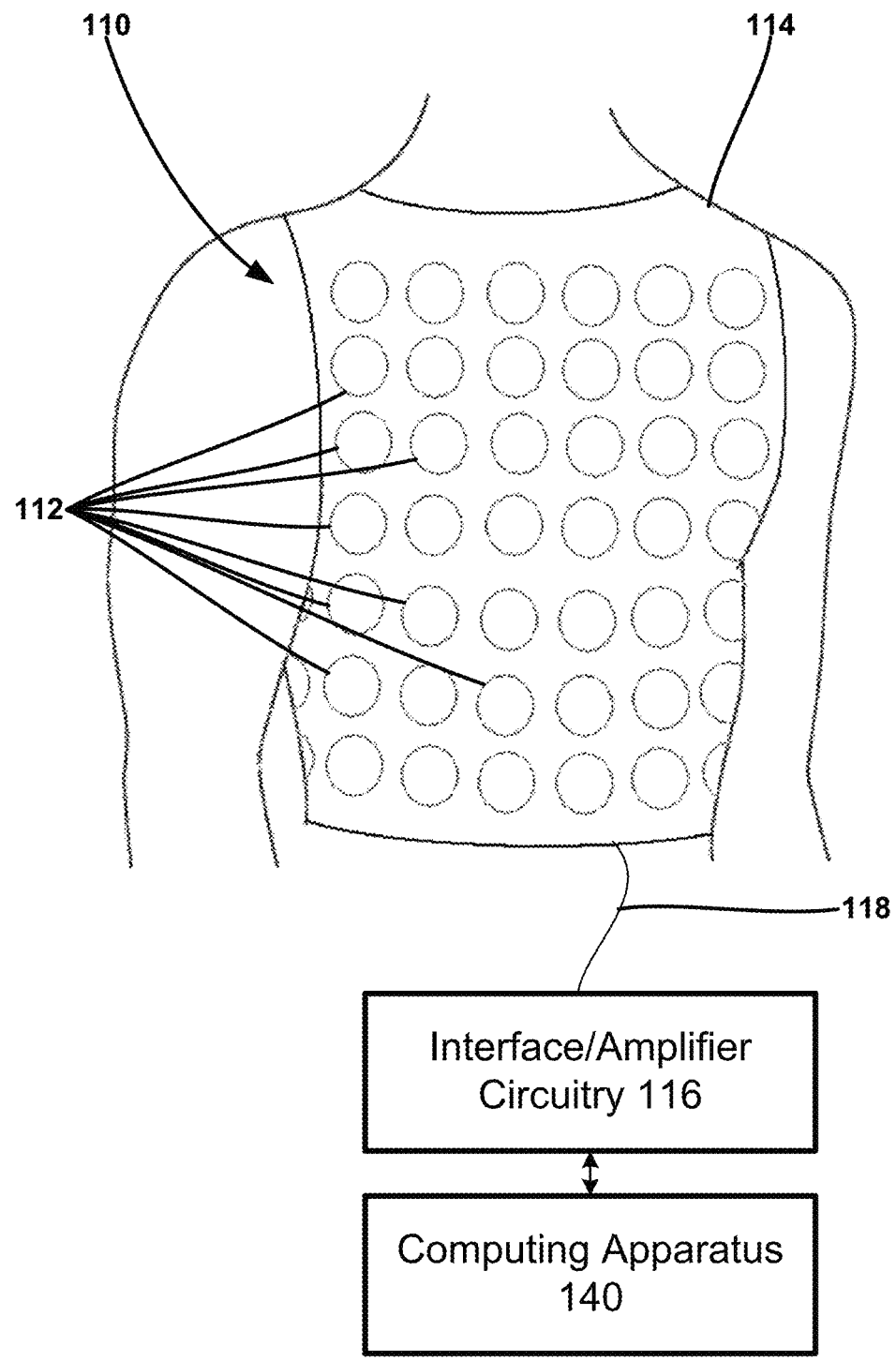

FIG. 3 illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of the patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 2, the electrode apparatus 110 of FIG. 3 may include interface/amplifier circuitry 116 electrically coupled to each of the electrodes 112 through a wired connection 118 and be configured to transmit signals from the electrodes 112 to computing apparatus 140. As illustrated, the electrodes 112 may be distributed over the torso of a patient 14, including, for example, the anterior, lateral, posterolateral, anterolateral, and posterior surfaces of the torso of the patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In one or more embodiments, the vest 114 may include 17 or more anterior electrodes positionable proximate the anterior torso of the patient, and 39 or more posterior electrodes positionable proximate the anterior torso of the patient. In some examples, there may be about 25 electrodes 112 to about 256 electrodes 112 distributed around the torso of the patient 14, though other configurations may have more or less electrodes 112.

As described herein, the electrode apparatus 110 may be configured to measure electrical information (e.g., electrical signals) representing different regions of a patient's heart. For example, activation times of different regions of a patient's heart can be approximated from surface electrocardiogram (ECG) activation times measured using surface electrodes in proximity to surface areas corresponding to the different regions of the patient's heart.

The exemplary systems, methods, and interfaces may be used to provide noninvasive assistance to a user in the evaluation of a patient's cardiac health or status, and/or the evaluation of cardiac therapy such as His bundle pacing therapy by use of the electrode apparatus 110 (e.g., cardiac therapy being presently-delivered to a patient during implantation or after implantation). Further, the exemplary systems, methods, and interfaces may be used to assist a user in the configuration of the cardiac therapy being delivered to a patient.

Figure 4:
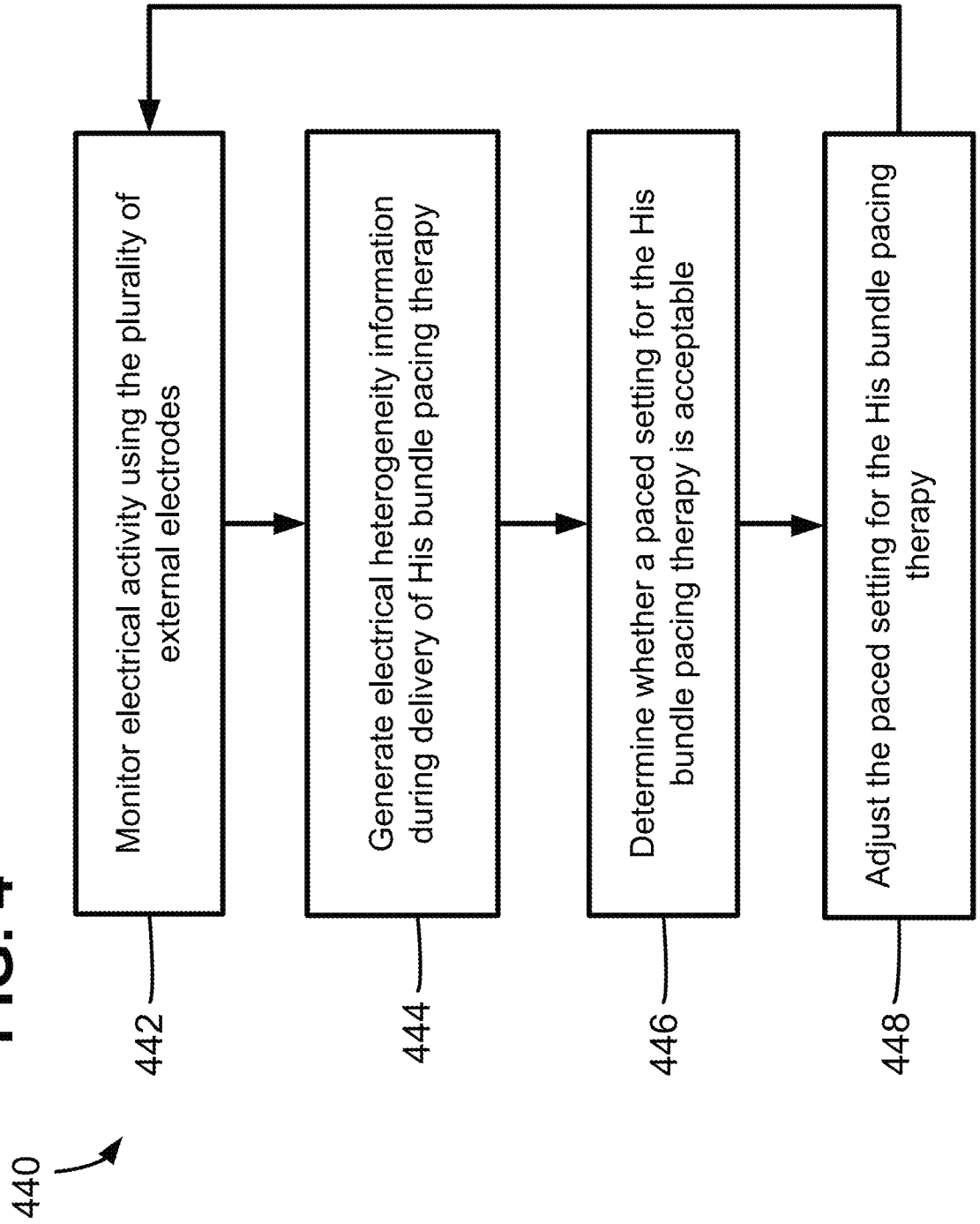
FIG. 4 is a block diagram of an exemplary method of evaluation of His bundle pacing therapy.

His bundle pacing can provide a more synchronized homogeneous activation of ventricles of the heart when compared to pacing from other areas of the ventricles. As an example, patients with atrial-ventricular (AV) block or prolonged AV timings that can lead to heart failure who have otherwise intact (e.g., normal) QRS can benefit from His bundle pacing therapy. In addition, as an example, heart failure patients with intrinsic ventricular conduction disorders His bundle pacing may provide a more beneficial activation. Proper placement of His bundle pacing can provide a more optimal activation of the ventricles for such patients. An exemplary method 440 of evaluation of His bundle pacing is illustrated in FIG. 4. The method 440 can include monitoring electrical activity using a plurality of external electrodes 442, such as electrodes 112 described herein with reference to FIGS. 1-3. The electrical activity can be monitored by a plurality of electrodes during His bundle pacing therapy or in the absence of His bundle pacing therapy. The monitored electrical activity can be used to evaluate His bundle pacing therapy to a patient using, e.g., the exemplary system described herein with respect to FIGS. 1-3. The electrical activity monitored using the ECG belt described above can be used to evaluate paced setting of the His bundle pacing therapy on the heart. As an example, a paced setting can be any one parameter or a combination of parameters including, but not limited to, electrode position, pacing polarity, pacing output, pacing pulsewidth, etc. Further, as an example, the location of the His bundle can include the high septum proximal to an AV groove. Moreover, pacing of the His bundle can be selective (e.g., involving stimulation of His bundle alone) or non-selective (e.g., combined pacing of His bundle and atrial and/or ventricular septum).

Further, body-surface isochronal maps of ventricular activation can be constructed using the monitored electrical activity during His bundle pacing therapy or in the absence of His bundle pacing therapy. The monitored electrical activity and/or the map of ventricular activation can be used to generate electrical heterogeneity information. The electrical heterogeneity information can include determining metrics of electrical heterogeneity.

The metrics of electrical heterogeneity can include a metric of standard deviation of activation times (SDAT) of electrodes on a left side of a torso of the patient and/or a metric of mean left ventricular activation time (LVAT) of electrodes on the left side of the torso of the patient. A metric of LVAT may be determined from electrodes on both the anterior and posterior surfaces. The metrics of electrical heterogeneity information can include a metric of mean right ventricular activation time (RVAT) of electrodes on the right side of the torso of the patient. A metric of RVAT may be determined from electrodes on both the anterior and posterior surfaces. The metrics of electrical heterogeneity can include a metric of mean total activation time (mTAT) taken from a plurality of electrode signals from both sides of the torso of the patient, or it may include other metrics (e.g., standard deviation, interquartile deviations, a difference between a latest activation time and earliest activation time) reflecting a range or dispersion of activation times on a plurality of electrodes located on the right side of the patient torso or left side of the patient torso, or combining both right and left sides of the patient torso.

The method 440 can include generating electrical heterogeneity information during delivery of His bundle pacing therapy at one or more His bundle paced setting 444. The electrical heterogeneity information can be generated using metrics of electrical heterogeneity. As an example, the metrics of electrical heterogeneity can include at least one of an SDAT, an LVAT, an RVAT, and an mTAT.

The method 440 can include determining whether one or more paced settings associated with the His bundle pacing therapy are acceptable 446. A paced setting can include a plurality of pacing parameters that can be determined to be acceptable if the patient's cardiac condition improves, if the His bundle pacing therapy is determined to be effectively capturing the His bundle, if a metric of electrical heterogeneity improves by a certain threshold compared to a baseline rhythm or therapy, if a metric of electrical heterogeneity is greater than or less than a particular threshold, if the location of the pacing therapy to excite the His bundle causes a particular pattern of excitation of the muscle fibers in the heart, etc. The paced setting can be determined to be acceptable in response to the His bundle pacing therapy using the paced setting being optimal, being beneficial, etc. A paced setting can include at least one of a pacing electrode position, a voltage, a pulse width, an intensity, a pacing polarity, a pacing vector, a pacing waveform, a timing of the pacing delivered relative to an intrinsic or paced atrial event, and/or a pacing location. A pacing vector can include any two or more pacing electrodes such as, e.g., a tip electrode to a can electrode, a tip electrode to a ring electrode etc., that are used to deliver the His bundle pacing therapy, etc. The pacing location can refer to the location of any of the one or more pacing electrodes that are positioned using a lead, a leadless device, and/or any device or apparatus configured to deliver His bundle pacing therapy.

In at least one embodiment, the determination of whether the paced setting is acceptable can be based on at least one metric of electrical heterogeneity generated from electrical activity of during His bundle pacing (and also, in some embodiments, during native conduction). The at least one metric can include at least one of an SDAT, an LVAT, and an RVAT. Further, AV conduction can be helpful in determining whether the paced settings of the His bundle pacing therapy are acceptable. In response to no AV conduction being present, the paced setting associated with the selected location for His bundle pacing therapy can be acceptable if at least one metric of electrical heterogeneity is below a threshold (or, in some examples, above a threshold). As an example, the paced setting can be acceptable in response to an SDAT generated during His bundle pacing therapy being below a selected threshold. The paced setting can be acceptable in response to an LVAT generated during His bundle pacing therapy being below a selected threshold. The paced setting can be acceptable in response to an RVAT generated during His bundle pacing therapy being below a selected threshold. In at least one embodiment, the paced setting can be acceptable in response to both the SDAT and the LVAT generated during His bundle pacing therapy being below selected threshold for each. As an example, the selected thresholds corresponding to an SDAT can be less than or equal to 25 milliseconds (ms). The selected threshold corresponding to an LVAT can be less than or equal to 35 ms. Further, the threshold to compare the metric of electrical heterogeneity, and which metric to use, can be based on characteristics of the AV conduction.

The method 440 can include adjusting a paced setting for His bundle pacing therapy 448. In at least one embodiment, the paced setting can be adjusted in response to the paced setting being unacceptable. In at least one embodiment, the paced setting can be adjusted in response to the paced setting being within an acceptable range but in order to determine whether the paced setting can be at a position within the acceptable range that is more beneficial, more useful, more functional, etc. for the His bundle pacing therapy. As an example, when the paced setting is a location that the His bundle pacing therapy is administered within a patient, the paced setting (e.g., location, depth of penetration of helical electrode, etc.) can be adjusted until the His bundle pacing therapy results in a metric of electrical heterogeneity is above or below a threshold metric of electrical heterogeneity. That is, the paced setting can be adjusted to assist in placement of a lead and/or other electrical device to administer the His bundle pacing therapy.

For example, pacing of the His bundle can utilize a pacing electrode that includes a 4 millimeter (mm) long helix, and the exemplary method 440 may be used to gradually titrate navigating the electrode up to 4 mm depth. More specifically, the pacing electrode may be partially screwed into, or attached to, a location proximate the His bundle, His bundle pacing may be performed, electrical activity may be monitored 442 during such His bundle pacing, electrical heterogeneity information may be generated 444, and it may be determined whether the pacing setting, which in this case, may be electrode location including depth, is acceptable 446. Next, the paced setting, which in this case may be a location including depth, may be adjusted 448. Thus, the pacing electrode may be screwed in, or positioned, deeper in tissue proximate the His bundle, and the method 440 may reiterate or be repeated. In other words, the exemplary method 440 may indicate to a doctor to gradually slow down turning of the helix electrode into a location proximate the His bundle.

Further, in one or more embodiments, a determination of whether the paced setting is acceptable can be based on a particular metric of electrical heterogeneity using an ECG belt. For example, when a paced setting is associated with a first metric value of electrical heterogeneity, an indication (e.g., a display, a prompt, etc.) to turn a pacing electrode helix a particular number of turns can be made (e.g., to adjust the depth of implant of the pacing electrode helix). In response to the paced setting being associated with a second metric value of electrical heterogeneity, an indication to stop turning the pacing electrode helix can be made. Furthermore, based on a metric of electrical heterogeneity, an indication of how many more turns of the pacing electrode helix can be indicated to assist in determining how much further to go with the pacing electrode helix. These indications can be displayed on a GUI of a monitor to assist in adjusting the paced setting and/or be on any number of display and/or notification devices.

In at least one example, the paced setting can be adjusted at intervals that correlate with a change in the metric of electrical heterogeneity until the metric of electrical heterogeneity is at or proximate a particular metric value. For instance, the adjusting of the paced setting can cause the metric of electrical heterogeneity to approach a particular threshold metric of electrical heterogeneity and, as the metric approaches the particular threshold, the rate at which the paced setting is adjusted can be slowed down. Put another way, as the metric of electrical heterogeneity is further from the particular threshold metric, the paced setting can be adjusted more quickly and as the metric of electrical heterogeneity gets closer to the particular threshold metric, the paced setting can be adjusted more slowly until the metric of electrical heterogeneity is at the particular threshold metric.

In at least one example, the paced setting (e.g., location including depth) can be adjusted until the His bundle pacing therapy results in a correction of bundle branch block (BBB). BBB can refer to a condition in which a delay and/or obstruction along a pathway that the electrical activity of the heart of the patient travels in order for the heart to properly beat. The delay and/or blockage may occur on the pathway that sends electrical impulses to the left or right side of the ventricles of the heart. The paced setting can be adjusted until the delay and/or blockage along the pathway is remedied, which can be indicated by a change in the metric of electrical heterogeneity, the metric of electrical heterogeneity being above or below a particular threshold, and/or any number of electrical information that may indicate that the BBB has been corrected. In at least one example, the paced setting can be adjusted until the metric of electrical heterogeneity indicating a delay and/or blockage of BBB reaches a particular threshold metric. The metric of electrical heterogeneity being at the particular threshold metric can indicate the BBB has been corrected. The paced setting can be adjusted at a greater rate while the metric of electrical heterogeneity is further from the particular threshold metric and adjusted at a slower rate as the metric of electrical heterogeneity gets closer to the particular threshold metric.

At least one characteristic of the AV conduction can include the presence and synchronicity of native AV conduction. If the native AV conduction is determined to be absent or very prolonged (e.g., greater than or equal to 300 ms), the paced setting associated with the selected location for His bundle pacing therapy can be acceptable in response to at least one metric of electrical heterogeneity being below a selected threshold. If the AV conduction is determined to be present and native AV conduction is found to be synchronized based on at least one of the electrical heterogeneity measures below a selected threshold, the paced setting associated with the selected location for His bundle pacing therapy can be acceptable in response to at least one metric of electrical heterogeneity being less than a selected percentage different than a corresponding metric of electrical heterogeneity generated during AV conduction in the absence of pacing therapy.

More specifically in response to the metrics of the native AV conduction being below a threshold (e.g., a first threshold for SDAT, a second threshold for LVAT, etc.), and therefore considered synchronous, the paced setting associated with the selected location for His bundle pacing therapy can be acceptable in response to 1) at least one metric of electrical heterogeneity being below a selected threshold, and 2) at least one metric of electrical heterogeneity being less than a selected percentage different than a corresponding metric of electrical heterogeneity generated during AV conduction in the absence of pacing therapy. As an example, the paced setting can be acceptable in response to an SDAT during native AV conduction being below a selected first threshold, an LVAT during native AV conduction being below a selected second threshold, and the SDAT during native AV conduction and an SDAT during His bundle pacing therapy and between the LVAT during native AV conduction and an LVAT during His bundle pacing therapy is less than a selected percentage difference. In at least some examples, the first threshold 25 ms. In at least some examples, the second threshold is 35 ms. In at least some examples, the selected percentage is 5%. However, selected percentages are not limited to this example.

More specifically, in response to the metrics of the AV conduction being above corresponding thresholds (e.g., a first threshold for SDAT, a second threshold for LVAT, etc.), and therefore considered asynchronous (or dyssynchronous), the paced setting associated with the selected location for His bundle pacing therapy can be acceptable in response to at least one metric of electrical heterogeneity generated during His bundle pacing being below a selected threshold. In the alternative, the paced setting associated with the selected location for His bundle pacing therapy can be acceptable in response to at least one metric of electrical heterogeneity during pacing being reduced by a selected percentage in relation to a corresponding metric of electrical heterogeneity generated during native AV conduction. As an example, the SDAT during pacing can be reduced by the selected percentage from the SDAT during AV conduction for the paced setting to be acceptable. The LVAT during pacing can be reduced by a selected percentage from the LVAT during AV conduction for paced setting to be acceptable. An example percentage in relation to the SDAT can be a 20% reduction. An example percentage in relation to LVAT can be a 20% reduction. However, selected percentages are not limited to this percent of reduction.

In at least one embodiments, the electrical heterogeneity information can be generated while delivering His bundle pacing cardiac therapy using a selected first paced setting. In response to the selected first paced setting being determined to be an unacceptable paced setting, a selected second paced setting can be used. As an example, the first paced setting can include a first location near the His bundle. In response to the first location not being indicated as an acceptable location evaluated at one or more pacing voltages, polarities, or timings, a second location can be used for delivering the His bundle pacing therapy.

Lead placement at a site at, or in close proximity to, the His bundle can be determined using the method described above. In at least one example, the method can be performed during implant placement. A decision-making process to determine whether to use the tested location (e.g., a first location) or to try for an additional location (e.g., a second location) for better results could be based on an automated system. As an example, parameters can be set to indicate whether the location is acceptable and when those parameters are met, the system automatically accepts the paced settings (e.g., location for His bundle pacing using a lead). In response to a determination that the His bundle pacing therapy is not acceptable (e.g., the His bundle paced setting used to deliver the His bundle pacing therapy), the His bundle paced setting can be changed. In response to changing the paced setting, a determination of whether the changed His bundle paced setting for the His bundle pacing therapy is acceptable based on the electrical heterogeneity information generated from the electrical activity using the plurality of external electrodes during delivery of His bundle pacing therapy using the changed His bundle paced setting can be performed. In at least one example, the data from the metrics of electrical heterogeneity can be provided to a clinician and the clinician can make the decision whether to accept the paced setting (e.g., a location for His bundle pacing using a lead).

In at least one embodiment, a metric of electrical heterogeneity used to determine whether a paced setting is acceptable can be used to compare His bundle pacing therapy to cardiac resynchronization therapy (CRT). A metric of electrical heterogeneity while performing CRT can be generated. Then, as an example, the metric of electrical heterogeneity for CRT can be compared to the metric of electrical heterogeneity for His bundle pacing.

Figure 5:
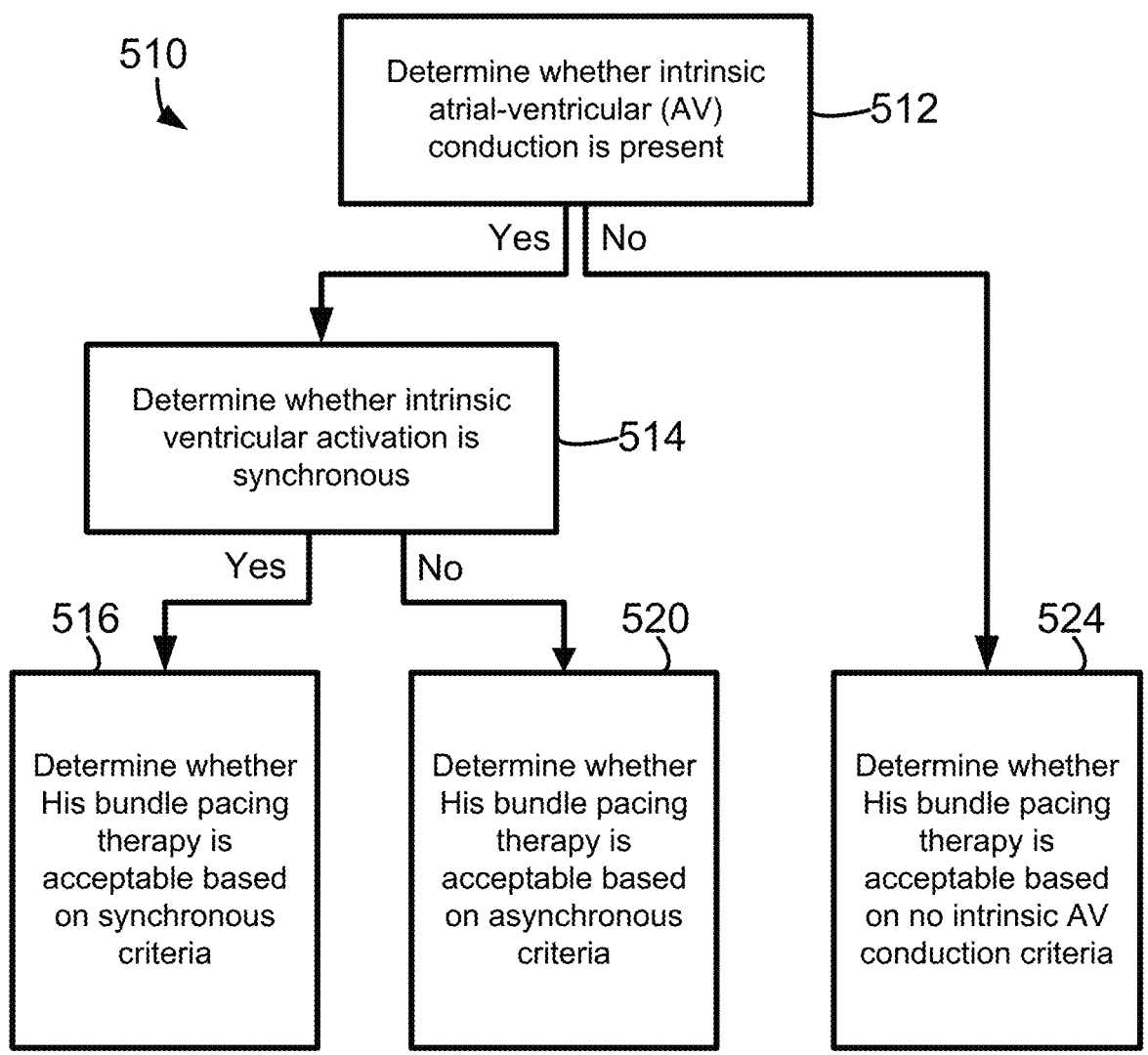
FIG. 5 is a block diagram of another exemplary method of evaluation of His bundle pacing therapy.

FIG. 5 is a detailed block diagram of another exemplary method 510 of evaluating His bundle pacing therapy. The method 510 can include determining whether atrial-ventricular (AV) conduction is present 512. The determination of whether AV conduction is present can be conducted during native AV conduction in the absence of pacing therapy. In at least one embodiment, monitored electrical activity from external electrodes during non-pacing can be used to determine native (or inherent and in the absence of pacing) AV conduction. The AV conduction can be determined to be present if the native AV conduction time (measured, as an example, by a PR interval on the ECG or timing from an atrial event sensed within the atrial chamber to an intrinsic ventricular event sensed within the ventricular chamber) is above a selected threshold (e.g., not zero or a certain amount above zero).

In response to determining that AV conduction is present (Yes), the method 510 can include determining whether the AV conduction is synchronous (or asynchronous) 514. The AV conduction can be determined to be synchronous by evaluating electrical cardiac heterogeneity generated using electrical activity monitored by the external electrodes described herein. For example, the method 510 can include determining whether one or more metrics of electrical heterogeneity (EH) are below a threshold to determine, or conclude, that the AV conduction is synchronous or asynchronous 514. The one or more metrics of electrical heterogeneity can be SDAT and LVAT. For example, the threshold for SDAT can be within a range of about 5 milliseconds (ms) to about 45 ms, and the threshold for LVAT can be within a range of about 10 ms to about 50 ms. As an example, the threshold for SDAT may be 25 ms and the threshold for LVAT may be 35 ms. Thus, if the SDAT is less than or equal to 25 ms, and the LVAT is less than or equal to 35 ms, it may be determined that the AV conduction is synchronous. Conversely, if the SDAT is greater than 25 ms or the LVAT is greater than 35 ms, it may be determined that the AV conduction is asynchronous.

Next, depending on whether the intrinsic AV conduction was determined to be synchronous or not, the exemplary method 510 may evaluate the His bundle pacing therapy using, for example, one or more metrics of electrical heterogeneity generated using a plurality of electrode signals captured by the external electrodes described herein. The evaluation may be different depending whether the intrinsic AV conduction was determined to be synchronous or not. For instance, different tests or comparisons may be performed and/or different thresholds may be used.

For example, if the intrinsic AV conduction was determined to be synchronous, the exemplary method 510 may determine whether the His bundle pacing therapy is acceptable, or more specifically, whether one or more parameters of His bundle pacing therapy are acceptable, using synchronous criteria 516. The synchronous criteria can include comparisons of one or more metrics of electrical heterogeneity generated from electrical activity monitored using the external electrodes described herein during the delivery of His bundle pacing therapy and/or in the absence of His bundle pacing therapy. A baseline metric can refer to a metric generated during native AV conduction in the absence of His bundle pacing therapy to a patient or a metric generated during previous His bundle pacing therapy using different settings or parameters or a metric generated during other cardiac pacing (e.g., more conventional cardiac pacing such as right ventricular pacing). A therapy metric can refer to a metric generated while delivering His bundle pacing therapy to a patient.

The one or more metrics used to determine whether the His bundle pacing therapy is acceptable when intrinsic AV conduction is determined to be synchronous may be SDAT and LVAT. Each of the metrics may be compared to threshold values, and a comparison of each metric during delivery of His bundle pacing therapy to the patient and without delivery of His bundle pacing therapy may be performed. For example, in at least one embodiment, the threshold for SDAT can be within a range of about 5 milliseconds (ms) to about 45 ms, and the threshold for LVAT can be within a range of about 10 ms to about 50 ms. As an example, the threshold for SDAT may be 25 ms and the threshold for LVAT may be 35 ms. Thus, if the SDAT is less than or equal to 25 ms, and the LVAT is less than equal to 35 ms, it may be determined that the His bundle pacing therapy is acceptable. Conversely, if the SDAT is greater than 25 ms or the LVAT is greater than 35 ms, it may be determined that the His bundle pacing therapy is unacceptable. Other thresholds that may be used for SDAT can include 20 ms, 22 ms, 24 ms, 26 ms, 28 ms. Other thresholds that may be used for LVAT are 20 ms, 25 ms, 30 ms, 35 ms, 40 ms, 45 ms.

Further, for example, in at least one embodiment, a relative percentage difference between one or more metrics of EH generated during delivery of His bundle pacing therapy and one or more baseline metrics of EH (either in the absence of delivery of His bundle pacing therapy or during previous settings of His bundle pacing therapy) may be compared to a threshold percentage. His bundle pacing may be considered acceptable if the relative percentage difference in EH with pacing and EH without pacing (measured relative to EH without pacing) is less than or equal to this percentage threshold. More specifically, in at least one embodiment, the one or more metrics of EH may be SDAT and LVAT, and the selected percentage threshold may be between about 1% to about 15%. In at least one embodiment, the selected percentage threshold for the absolute relative difference in EH with and without His bundle pacing is 5%. In one or more other embodiments the selected percentage may be less than or equal to 2%, less than or equal to 3%, less than or equal to 6%, less than or equal to 9%, less than or equal to 10%, less than or equal to 15%, etc.

In at least one embodiment, the threshold percentage is 5% for each of SDAT and LVAT. Thus, in this embodiment, if the change in SDAT from intrinsic conduction to His bundle pacing therapy is less than or equal to 5% and the change in LVAT from intrinsic conduction to His bundle pacing therapy is less than or equal to 5%, it may be determined that the His bundle pacing therapy is acceptable. Conversely, if the change in SDAT from intrinsic conduction to His bundle pacing therapy is greater than 5% and the change in LVAT from intrinsic conduction to His bundle pacing therapy is greater than 5%, it may be determined that the His bundle pacing therapy is unacceptable.

Additionally, although the comparison of EH metrics to thresholds and the comparison of the percentage difference between EH metrics generated during delivery of His bundle pacing therapy and EH baseline metrics are described separately, it is to be understood that each process may be used by itself or together to determine whether the His bundle pacing therapy is acceptable (or more specifically, whether one or more parameters of the His bundle pacing therapy are acceptable) 516.

For example, if the intrinsic AV conduction was determined to be asynchronous, the exemplary method 510 may determine whether the His bundle pacing therapy is acceptable, or more specifically, whether one or more parameters of His bundle pacing therapy are acceptable, using asynchronous criteria 520. The asynchronous criteria can include comparisons of one more metrics of electrical heterogeneity generated from electrical activity monitored using the external electrodes described herein during the delivery of His bundle pacing therapy and/or in the absence of His bundle pacing therapy.

The one or more metrics used to determine whether the His bundle pacing therapy is acceptable when intrinsic AV conduction is determined to be asynchronous may be SDAT and LVAT. Each of the metrics may be compared to threshold values, and a comparison of each metric during delivery His bundle pacing therapy to the patient and without delivery of His bundle pacing therapy may be performed. For example, in at least one embodiment, the threshold for SDAT can be within a range of about 5 milliseconds (ms) to about 45 ms, and the threshold for LVAT can be within a range of about 10 ms to about 50 ms. As an example, the threshold for SDAT may be 25 ms and the threshold for LVAT may be 35 ms. Thus, if during pacing, the SDAT is less than or equal to 25 ms, and the LVAT is less than equal to 35 ms, it may be determined that the His bundle pacing therapy is acceptable. Conversely, if the SDAT is greater than 25 ms or the LVAT is greater than 35 ms, it may be determined that the His bundle pacing therapy is unacceptable. Other thresholds that may be used for SDAT can include 20 ms, 22 ms, 24 ms, 26 ms, and 28 ms. Other thresholds that may be used for LVAT can include 20 ms, 25 ms, 30 ms, 35 ms, 40 ms, and 45 ms.

Further, for example, in at least one embodiment, a percentage reduction between one or more metrics of EH generated during delivery of His bundle pacing therapy and one or more baseline metrics of EH (either in the absence of delivery of His bundle pacing therapy or during previous settings of His bundle pacing therapy) may be compared to a threshold percentage. More specifically, in at least one embodiment, the one or more metrics of EH may be SDAT and LVAT, and the selected percentage threshold for reduction in EH during pacing compared to without pacing may be anywhere between 10 and 30%.

In at least one embodiment, the threshold percentage is 20% for SDAT. Thus, in this embodiment, if the change in SDAT from intrinsic conduction to His bundle pacing therapy is reduced by greater than or equal to 20% relative to intrinsic, it may be determined that the His bundle pacing therapy is acceptable. Conversely, if the change in SDAT from intrinsic conduction to His bundle pacing therapy is reduced less than 20%, it may be determined that the His bundle pacing therapy is unacceptable.

In at least one embodiment, the threshold percentage is 10% for SDAT and the threshold percentage is 20% for LVAT. Thus, in this embodiment, if the change in SDAT from intrinsic conduction to His bundle pacing therapy is reduced by greater than or equal to 10% and the change in LVAT from intrinsic conduction to His bundle pacing therapy is reduced by greater than or equal to 20%, it may be determined that the His bundle pacing therapy is acceptable. Conversely, if the change in SDAT from intrinsic conduction to His bundle pacing therapy is reduced by less than 10% or the change in LVAT from intrinsic conduction to His bundle pacing therapy is reduced by less than 20%, it may be determined that the His bundle pacing therapy is acceptable.

Additionally, although the comparison of EH metrics to thresholds and the comparison of the percentage difference between EH metrics generated during delivery of His bundle pacing therapy and EH baseline metrics are described separately, it is to be understood that each process may be used by itself or together to determine whether the His bundle pacing therapy is acceptable (or more specifically, whether one or more parameters of the His bundle pacing therapy are acceptable) 520.

In response to determining that intrinsic AV conduction is not present (No), the method can include determining whether the His bundle pacing therapy is acceptable, or more specifically, whether one or more parameters of His bundle pacing therapy are acceptable, based on no intrinsic AV conduction criteria 524. The no intrinsic AV conduction criteria can include comparisons of one more metrics of electrical heterogeneity generated from electrical activity monitored using the external electrodes described herein during the delivery of His bundle pacing therapy against predetermined thresholds.

For example, one metric of EH that can be used in the determination 524 is SDAT, and the SDAT may be compared to a threshold value that may be less than or equal to 25 ms. Further, for example, another metric of EH that can be used in the determination 524 is LVAT, and the LVAT can be compared to another threshold value that may be less than or equal to 35 ms. In other embodiments, the threshold value for the SDAT can be within a range of about 5 ms to about 40 ms, and the threshold value for the LVAT can be within a range of about 10 ms to about 45 ms. Thus, in this example, determining whether the His bundle pacing therapy is acceptable 425 may include comparing the SDAT and LVAT, both generated from electrical activity during His bundle pacing, to various thresholds. More specifically, if the SDAT is less than or equal to 25 milliseconds and the LVAT is less than or equal to 35 milliseconds, it may be determined that the paced setting for His bundle pacing therapy is acceptable 526. Conversely, if the SDAT is greater than 25 milliseconds or the LVAT is greater than 35 milliseconds, it may be determined that the paced setting for His bundle pacing therapy is unacceptable 528.

Figure 6:
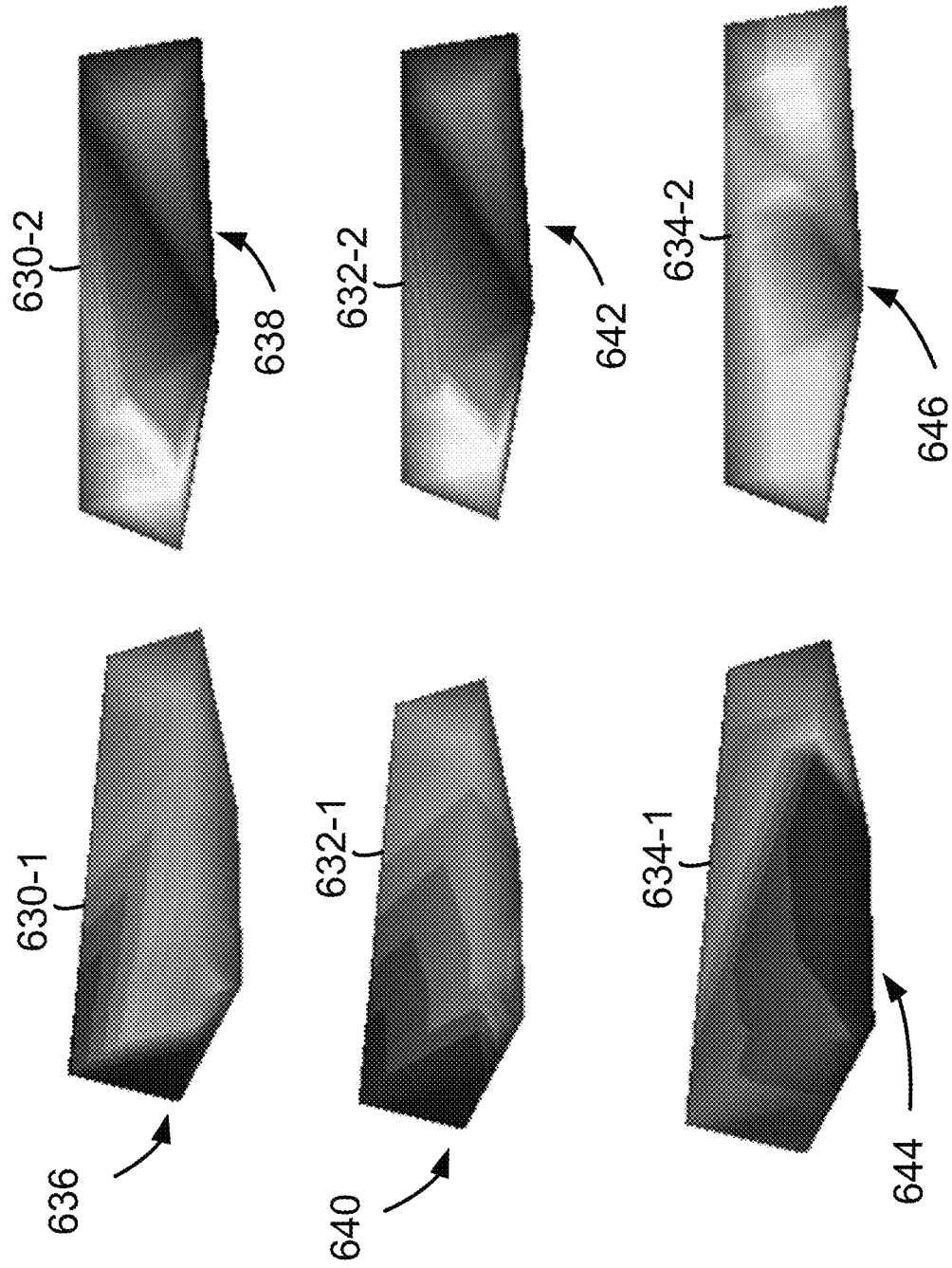
FIG. 6 is an exemplary illustration of a plurality of cardiac electrical activation time maps generated from electrical activity during His bundle pacing therapy.

FIG. 6 is an exemplary illustration of isochronal maps representing electrical activation determined from a plurality of external surface electrodes. 630-1, 632-1, 634-1 are maps from the anterior aspect of the torso, 630-2, 632-2, 634-2 are the corresponding maps on the posterior aspect. The pair of isochronal maps 630-1 and 630-2 represent a left bundle dominant capture as the early activated portion 638 is larger for the posterior aspect (630-2) than for the early activated portion 636 for the anterior aspect (630-1). As an example, a metric of electrical heterogeneity, such as RVAT, that indicates excitation of a cardiac right side would be larger in this illustration than a metric of electrical heterogeneity, such as LVAT, that indicates excitation of a cardiac left side. As illustrated in this example, the RVAT associated with pair of isochronal maps 630-1 and 630-2 is an RVAT of 36 ms. The LVAT associated with the pair of isochronal maps 630-1 and 630-2 is an LVAT of 15 ms.

Pair of isochronal maps 632-1 and 632-2 represent both a right and left bundle capture (non-dominant) as the early activated portions 640 and 642 of isochronal maps are present in both anterior and posterior aspects 632-1 and 632-2, respectively. The metrics of electrical heterogeneity, such as RVAT and LVAT, for both sides would be closer to equal in this case. As illustrated in this example, the RVAT associated with pair of isochronal maps 632-1 and 632-2 is an RVAT of 20 ms. The LVAT associated with the pair of isochronal maps 632-1 and 632-2 is an LVAT of 17 ms.

Pair of isochronal maps 634-1 and 634-2 represent a right bundle dominant capture as the early activated portion 644 is larger for the anterior aspect (634-1) than for the early activated portion 646 for the posterior aspect (634-2). In this example, a metric of electrical heterogeneity, such as LVAT, that indicates excitation of a cardiac left side (634-1) would be larger in this illustration than a metric of electrical heterogeneity, such as RVAT, that indicates excitation of a cardiac right side (e.g., 634-2). As illustrated in this example, the RVAT associated with pair of isochronal maps 634-1 and 634-2 is an RVAT of 22 ms. The LVAT associated with the pair of isochronal maps 634-1 and 634-2 is an LVAT of 47 ms.

As an example, full cardiac capture, which would indicate acceptable His bundle pacing therapy, could result when an RVAT value of less than or equal to 30 milliseconds (ms) and an LVAT value of less than or equal to 30 ms occurs together, indicating that excitation of both sides is spread out evenly and quick. An RVAT less than or equal to 30 ms and an LVAT of greater than or equal to 30 ms would indicate a partial capture with a dominant right-side capture, which may indicate less acceptable His bundle pacing therapy than full capture. An RVAT greater than or equal to 30 ms and an LVAT of less than or equal to 30 ms would indicate a partial capture with a dominant left side capture, which may also indicate less acceptable His bundle pacing therapy than full capture. An RVAT greater than or equal to 30 ms and an LVAT greater than or equal to 30 ms would indicate a partial capture of both sides with no dominant side or lack of His bundle capture (e.g., may be capturing just the septum without actually stimulating the His bundle), which may indicate less acceptable His bundle pacing therapy than full capture. As an example, His bundle pacing therapy can be administered and the above method performed until a full capture of both cardiac sides are achieved, and thus, the His bundle pacing therapy is acceptable. In addition, when full capture is not achieved, the maps and the RVAT and LVAT metrics can provide the information on the difference grades of His bundle capture and can help accordingly set a paced setting, e.g., if both RVAT and LVAT are greater than 30 ms, the electrode position may be altered to engage the His bundle, whereas if partial capture of His bundle is achieved, the pacing voltage may be increased to achieve full capture, etc.

The exemplary systems, methods, and graphical user interfaces described herein may be used with respect to the implantation and configuration of an implantable medical device (IMD) and/or one or more leads configured to be located proximate one or more portions of a patient's heart, e.g., proximate the His bundle. For example, the exemplary systems, methods, and interfaces may be used in conjunction with an exemplary therapy system 10 described herein with reference to FIGS. 7-11.

Figure 7:
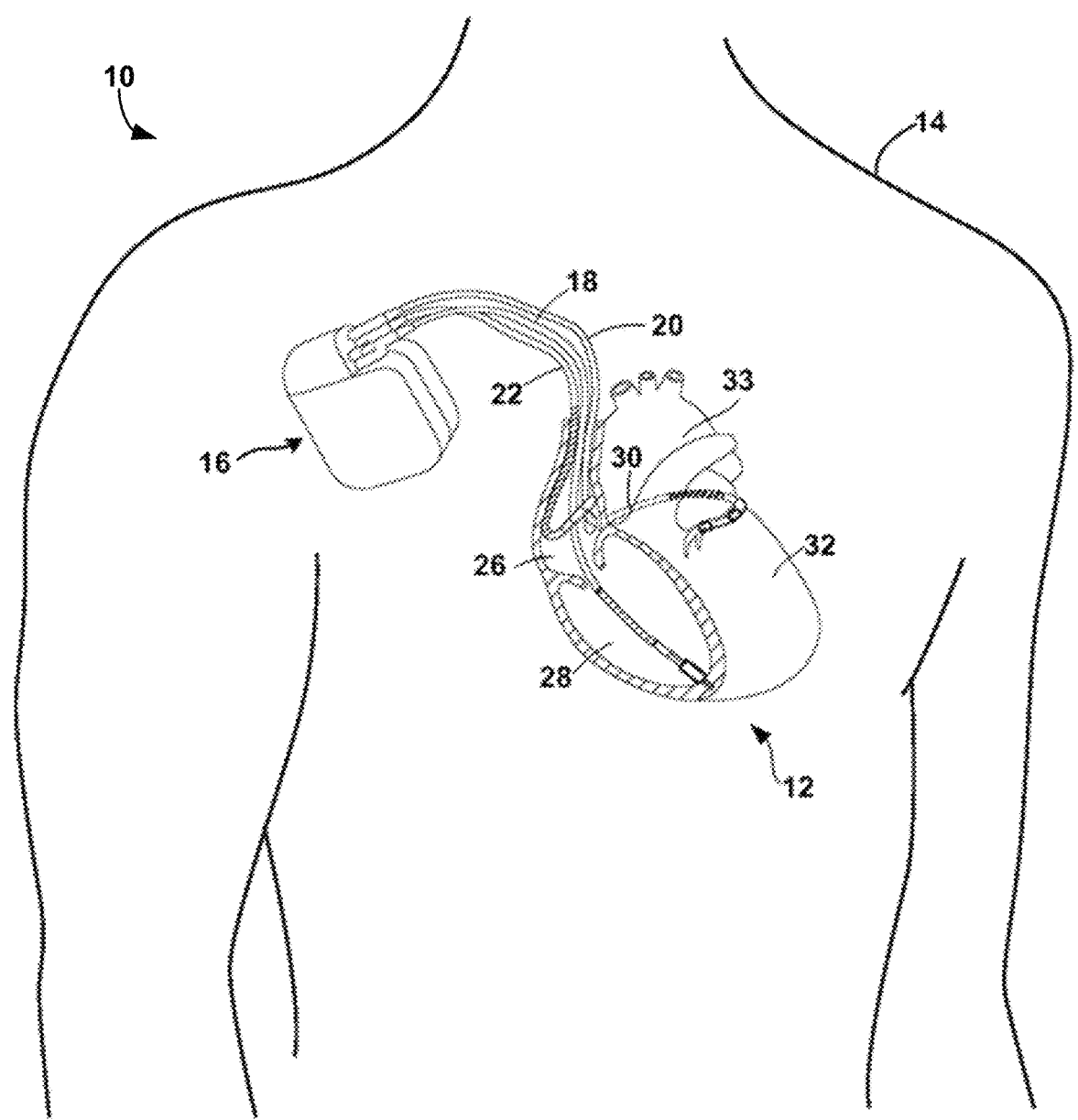
FIG. 7 is a diagram of an exemplary system including an exemplary implantable medical device (IMD).

FIG. 7 is a conceptual diagram illustrating an exemplary therapy system 10 that may be used to deliver pacing therapy to a patient 14 such as, for example, His bundle pacing therapy. Patient 14 may, but not necessarily, be a human. The therapy system 10 may include an implantable medical device 16 (IMD), which may be coupled to leads 18, 20, 22. The IMD 16 may be, e.g., an implantable pacemaker, cardioverter, and/or defibrillator, that delivers, or provides, electrical signals (e.g., paces, etc.) to and/or senses electrical signals from the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 7, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. In some examples, the IMD 16 provides His bundle pacing therapy (e.g., pacing pulses) to the heart 12 based on the electrical signals sensed within the heart 12. The IMD 16 may be operable to adjust one or more parameters associated with the His bundle pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripolar, or further multipolar. For example, a multipolar lead may include several electrodes that can be used for delivering pacing therapy. Hence, a multipolar lead system may provide, or offer, multiple electrical vectors to pace from.

A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy (such as, e.g., His bundle pacing) may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 8:
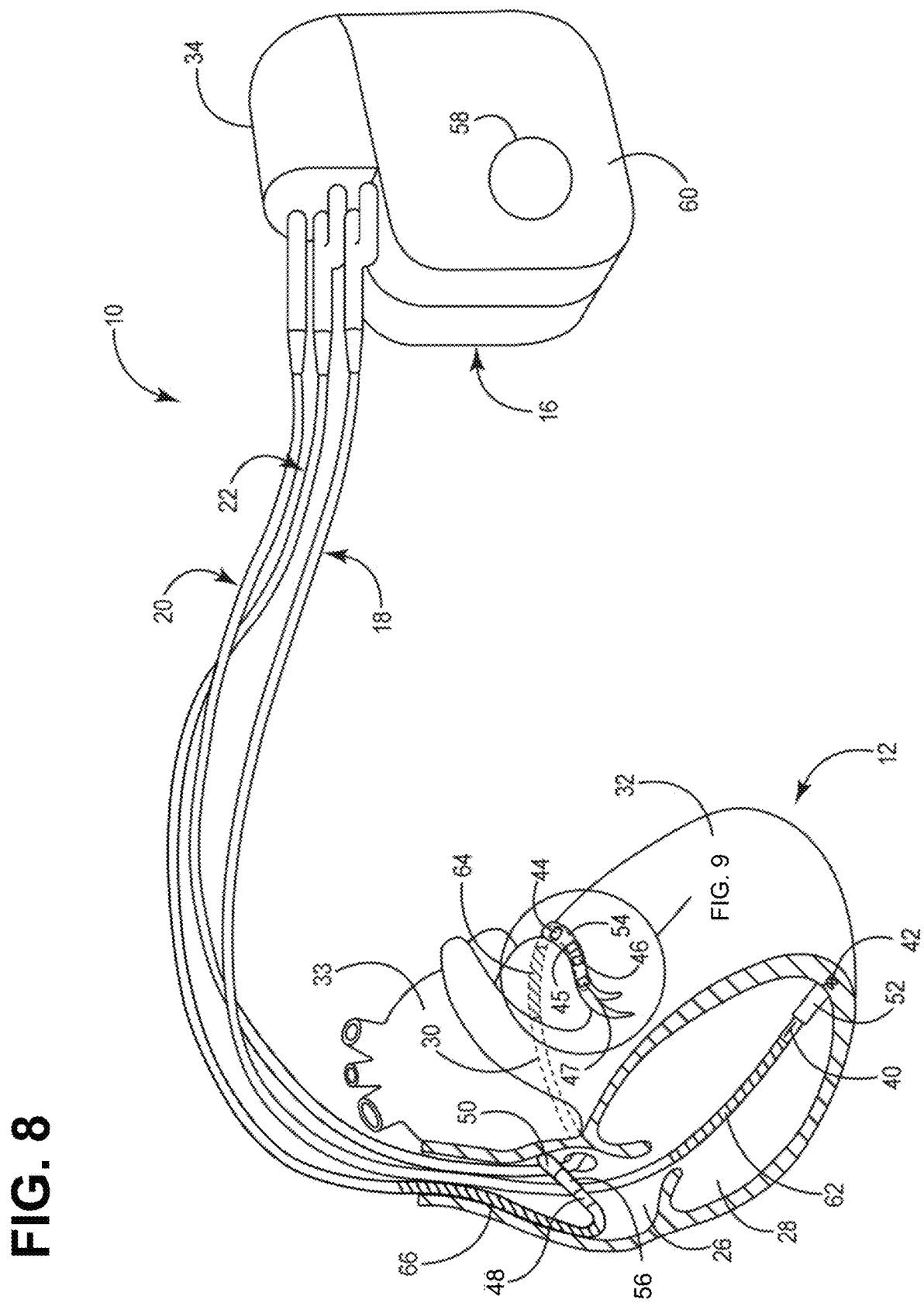
FIG. 8 is a diagram of the exemplary IMD of FIG. 7.
Figure 9:
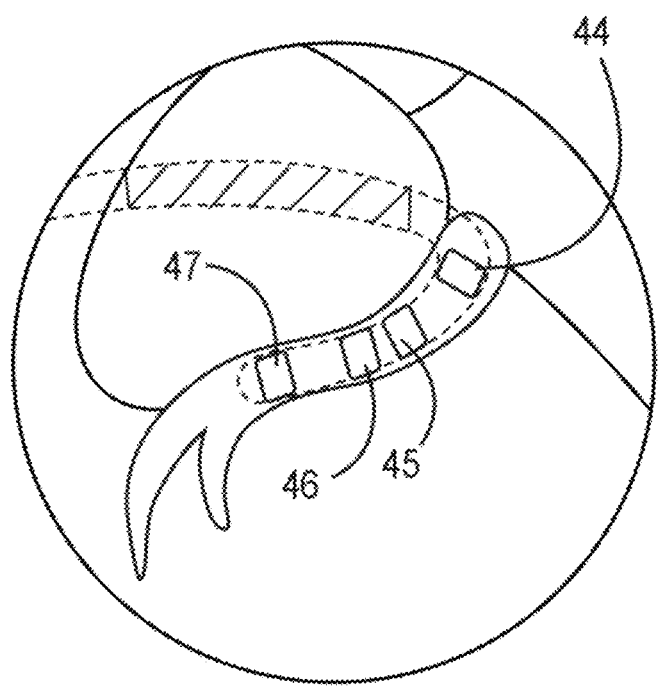
FIG. 9 is a diagram of an enlarged view of a distal end of the electrical lead disposed in the left ventricle of FIG. 8.

FIGS. 8-9 are conceptual diagrams illustrating the IMD 16 and the leads 18, 20, 22 of therapy system 10 of FIG. 7 in more detail. The leads 18, 20, 22 may be electrically coupled to a therapy delivery module (e.g., for delivery of His bundle pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, bipolar electrodes 44, 45, 46, 47 are located proximate to a distal end of the lead 20 and bipolar electrodes 48, 50 are located proximate to a distal end of the lead 22.

The electrodes 40, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to a respective one of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance, e.g., of about 21 millimeters (mm), away from electrode 45, electrodes 45 and 46 may be spaced a distance, e.g. of about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 8, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48, 50 may be used for unipolar sensing or pacing in combination with the housing electrode 58. It is generally understood by those skilled in the art that other electrodes can also be selected to define, or be used for, pacing and sensing vectors. Further, any of electrodes 40, 42, 44, 45, 46, 47, 48, 50, 58, when not being used to deliver pacing therapy (such as e.g., His bundle pacing therapy), may be used to sense electrical activity during pacing therapy.

As described in further detail with reference to FIG. 8, the housing 60 may enclose a therapy delivery module that may include a stimulation generator for generating cardiac pacing pulses and defibrillation or cardioversion shocks, as well as a sensing module for monitoring the electrical signals of the patient's heart (e.g., the patient's heart rhythm). The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58, or defibrillation electrode-to-housing electrode vector).

The configuration of the exemplary therapy system 10 illustrated in FIGS. 7-11 is merely one example. In other examples, the therapy system may include epicardial leads and/or patch electrodes instead of or in addition to the transvenous leads 18, 20, 22 illustrated in FIG. 7. Additionally, in other examples, the therapy system 10 may be implanted in/around the cardiac space without transvenous leads (e.g., leadless/wireless pacing systems) or with leads implanted (e.g., implanted transvenously or using approaches) into the left chambers of the heart (in addition to or replacing the transvenous leads placed into the right chambers of the heart as illustrated in FIG. 7). Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

Figure 10:
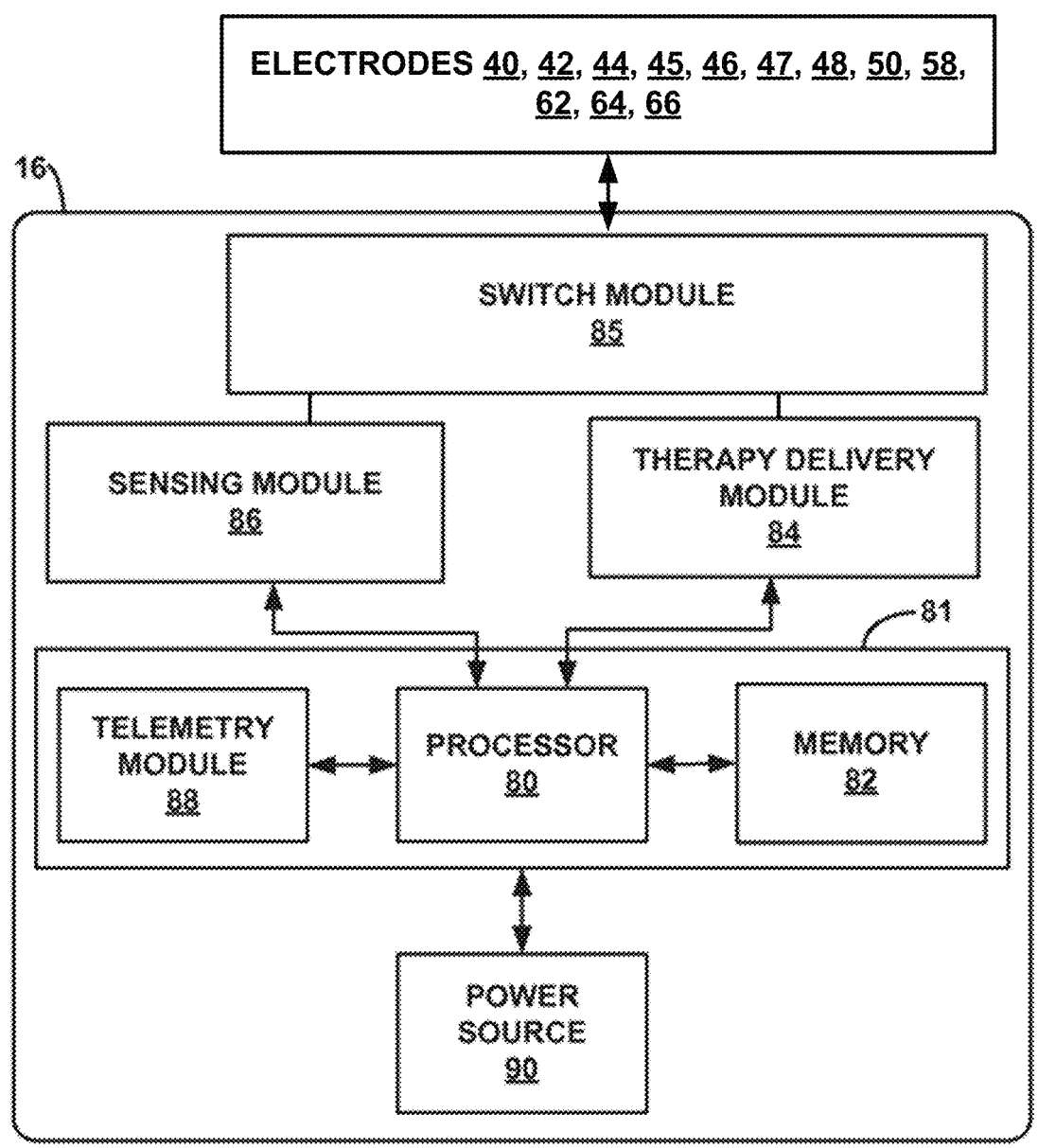
FIG. 10 is a block diagram of an exemplary IMD, e.g., of the systems of FIGS. 7-9.
Figure 11:
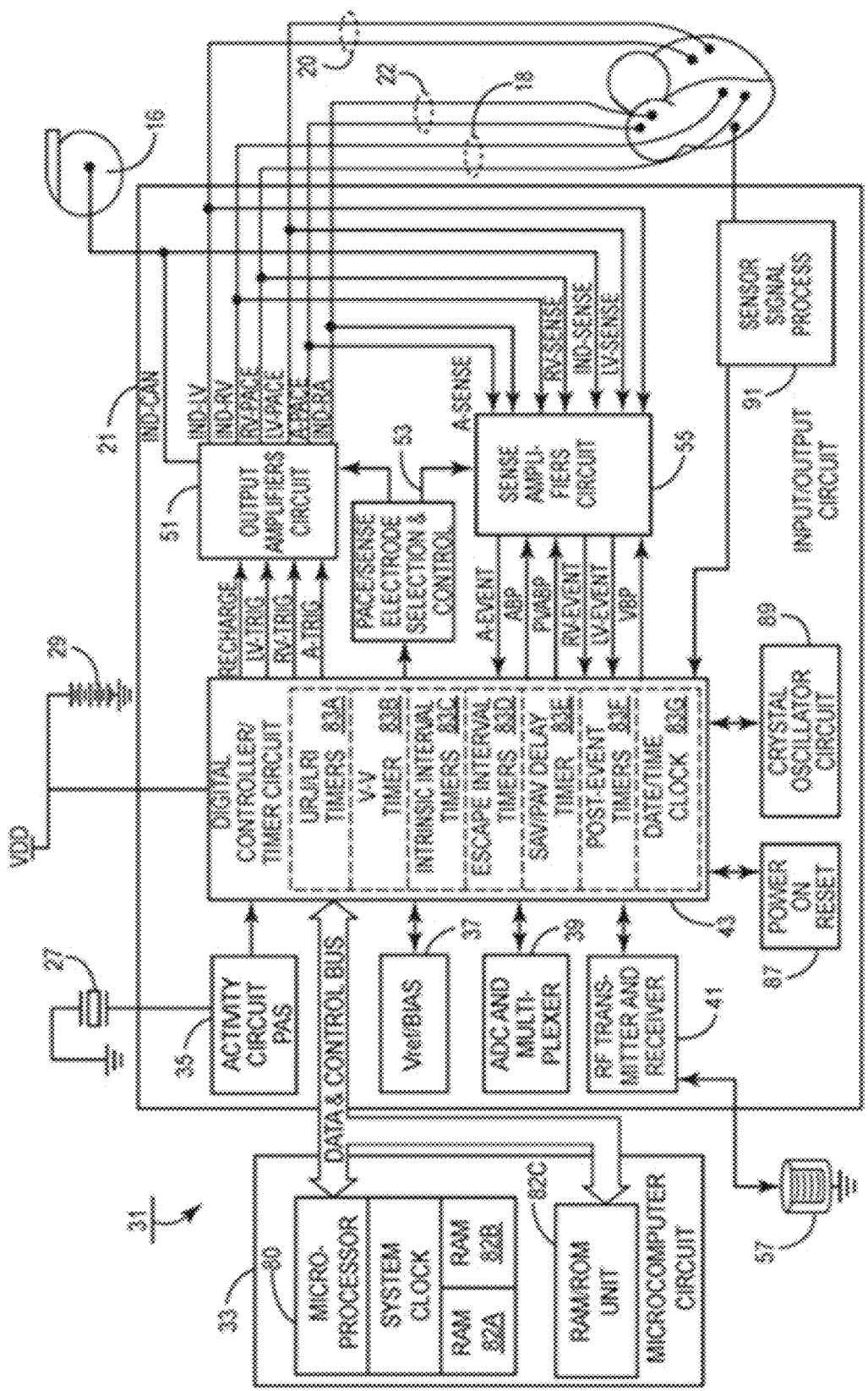
FIG. 11 is another block diagram of an exemplary IMD (e.g., an implantable pulse generator) circuitry and associated leads employed in the systems of FIGS. 7-9.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

FIG. 10 is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random-access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, VV delays, pacing pulses with the amplitudes, pulse widths, frequency, or electrode polarities, etc., which may be specified by one or more selected therapy programs (e.g., AV and/or VV delay adjustment programs, His bundle pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as His bundle pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, 22 and/or helical tip electrodes 42, 50 of leads 18, 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for His bundle pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a bipolar or multipolar pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

FIG. 11 is another embodiment of a functional block diagram for IMD 16. FIG. 11 depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a bi-ventricular DDD/R type known in the pacing art. In turn, the sensor signal processing circuit 91 indirectly couples to the timing circuit 43 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 43, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21 while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21. Analog-to-digital converter (ADC) and multiplexer circuit 39 digitize analog signals and voltage to provide, e.g., real time telemetry of cardiac signals from sense amplifiers 55 for uplink transmission via RF transmitter and receiver circuit 41. Voltage reference and bias circuit 37, ADC and multiplexer 39, power-on-reset circuit 87, and crystal oscillator circuit 89 may correspond to any of those used in exemplary implantable cardiac pacemakers.

If the IPG is programmed to a rate responsive mode, the signals output by one or more physiologic sensors are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer. The output signal of the patient activity sensor 27 may be processed and used as a RCP. Sensor 27 generates electrical signals in response to sensed physical activity that are processed by activity circuit 35 and provided to digital controller/timer circuit 43. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which is incorporated herein by reference in its entirety. Similarly, the exemplary systems, apparatus, and methods described herein may be practiced in conjunction with alternate types of sensors such as oxygenation sensors, pressure sensors, pH sensors, and respiration sensors, for use in providing rate responsive pacing capabilities. Alternately, QT time may be used as a rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities may include the ability to transmit stored digital information, e.g., operating modes and parameters, EGM histograms, and other events, as well as real time EGMs of atrial and/or ventricular electrical activity and marker channel pulses indicating the occurrence of sensed and paced depolarizations in the atrium and ventricle.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 43 and A-EVENT, RV-EVENT, and LV-EVENT signals generated by sense amplifiers circuit 55, among others. The specific values of the intervals and delays timed out by digital controller/timer circuit 43 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals, V-V delay intervals, and the energy delivered to each ventricle and/or atrium.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 43 operates under the general control of the microcomputer 33 to control timing and other functions within the pacing circuit 21 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F times out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, VV delays, post-ventricular time periods, and post-atrial time periods that vary with the sensor based escape interval established in response to the RCP(s) and/or with the intrinsic atrial and/or ventricular rate.

The output amplifiers circuit 51 contains a RA pace pulse generator (and a LA pace pulse generator if LA pacing is provided), a RV pace pulse generator, a LV pace pulse generator, and/or any other pulse generator configured to provide atrial and ventricular pacing. In order to trigger generation of an RV-PACE or LV-PACE pulse, digital controller/timer circuit 43 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 43 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND-CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 43 controls sensitivity settings of the atrial and ventricular sense amplifiers 55.

The sense amplifiers may be uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV, and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 43. Similarly, left atrial depolarizations or P-waves in the LA-SENSE signal that are sensed by the LA sense amplifier, if provided, result in a LA-EVENT signal that is communicated to the digital controller/timer circuit 43. Ventricular depolarizations or R-waves in the RV-SENSE signal are sensed by a ventricular sense amplifier result in an RV-EVENT signal that is communicated to the digital controller/timer circuit 43. Similarly, ventricular depolarizations or R-waves in the LV-SENSE signal are sensed by a ventricular sense amplifier result in an LV-EVENT signal that is communicated to the digital controller/timer circuit 43. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

ILLUSTRATIVE EMBODIMENTS

Embodiment 1

A system comprising:
electrode apparatus comprising a plurality of external electrodes to monitor electrical activity from tissue of a patient; and
computing apparatus comprising processing circuitry and coupled to the electrode apparatus and configured to:
monitor electrical activity using the plurality of external electrodes;
generate His bundle electrical heterogeneity information based on the monitored electrical activity during delivery of His bundle pacing therapy at one or more His bundle paced settings, wherein the His bundle electrical heterogeneity information is representative of at least one of mechanical cardiac functionality and electrical cardiac functionality; and
determine whether one or more of the His bundle paced settings for the His bundle pacing therapy are acceptable based on the electrical heterogeneity information.

Embodiment 2

The system of embodiment 1, wherein the one or more His bundle paced settings comprise at least one of a voltage, a pulse width, a location for the His bundle pacing therapy, pacing polarity and vector, and number of pacing electrodes used.

Embodiment 3

The system of any one of embodiments 1 to 2, wherein the system further comprises a His bundle pacing therapy apparatus comprising at least one implantable electrode, wherein the system is configured to assist a user in selecting an implant location for the at least one implantable electrode to deliver the His bundle pacing therapy.

Embodiment 4

The system of any one of embodiments 1 to 3, wherein the plurality of external electrodes comprises surface electrodes positioned in an array configured to be located proximate the skin of a torso of the patient.

Embodiment 5

The system of any one of embodiments 1 to 4, wherein the electrical heterogeneity information comprises a metric of electrical heterogeneity, wherein the determining whether the one or more of the His bundle paced settings for the His bundle pacing therapy are acceptable comprises:
determining whether intrinsic atrial ventricular (AV) conduction is not present; and
in response to determining that the intrinsic AV conduction is not present, determining that the one or more His bundle paced settings for the His bundle pacing therapy are acceptable if the metric of electrical heterogeneity is less than or equal to a threshold.

Embodiment 6

The system of any one of embodiments 1 to 6, wherein the determining whether the one or more of the His bundle paced settings for the His bundle pacing therapy are acceptable comprises:
determining whether intrinsic atrial ventricular (AV) conduction is present; and
in response to determining that the intrinsic AV conduction is present, determining whether intrinsic ventricular activation is synchronous by comparing at least one of the metrics of electrical heterogeneity during the intrinsic AV conduction to a threshold;
in response to determining that the intrinsic AV conduction is present and synchronous, determining whether the one or more His bundle paced settings for the His bundle pacing therapy are acceptable based on at least one of:
comparing the His bundle pacing therapy electrical heterogeneity information to a threshold; and
comparing baseline electrical heterogeneity information generated from electrical activity monitored in the absence of His bundle pacing therapy to the His bundle therapy electrical heterogeneity information generated from electrical activity monitored during the His bundle pacing therapy.

Embodiment 7

The system of embodiment 6, wherein each of the baseline and His bundle therapy electrical heterogeneity information comprises a metric of electrical heterogeneity,
wherein comparing baseline electrical heterogeneity information to His bundle therapy electrical heterogeneity information generated from electrical activity monitored during His bundle pacing therapy comprises comparing a difference between the metric of electrical heterogeneity of the His bundle therapy electrical heterogeneity information and the metric of electrical heterogeneity of the baseline electrical heterogeneity information to a threshold.

Embodiment 8

The system of any one of embodiments 1 to 7, wherein the determining whether the one or more of the His bundle paced settings for the His bundle pacing therapy are acceptable comprises:
determining whether intrinsic atrial ventricular (AV) conduction is present;
in response to determining that the intrinsic AV conduction is present, determining whether intrinsic ventricular activation is asynchronous by comparing at least one of the metrics of electrical heterogeneity during the intrinsic AV conduction to a threshold;
in response to determining that the intrinsic AV conduction is present and asynchronous, determining whether the one or more His bundle paced settings for the His bundle pacing therapy are acceptable based on at least one of:

comparing the electrical heterogeneity information to a threshold;

comparing baseline electrical heterogeneity information generated from electrical activity monitored in the absence of His bundle pacing therapy to His bundle therapy electrical heterogeneity information generated from electrical activity monitored during the His bundle pacing therapy.

Embodiment 9

The system of embodiment 8, wherein each of the baseline and the His bundle therapy electrical heterogeneity information comprises a metric of electrical heterogeneity, wherein comparing the baseline electrical heterogeneity information to the His bundle therapy electrical heterogeneity information generated from the electrical activity monitored during the His bundle pacing therapy comprises comparing a difference between the metric of electrical heterogeneity of the His bundle therapy electrical heterogeneity information and the metric of the baseline electrical heterogeneity information to a threshold.

Embodiment 10

The system of any one of embodiments 1 to 9, wherein the electrical heterogeneity information comprises at least one metric of electrical heterogeneity, wherein the at least one metric of electrical heterogeneity comprises at least one of a standard deviation of activation times (SDAT), a mean left ventricular activation time (LVAT), and a mean right ventricular activation time (RVAT).

Embodiment 11

The system of embodiment 10, wherein the determining whether the one or more His bundle paced settings for the His bundle pacing therapy are acceptable comprises comparing the at least one metric of electrical heterogeneity to a threshold.

Embodiment 12

A method comprising:

monitoring electrical activity from tissue of a patient using a plurality of external electrodes;

generating His bundle therapy electrical heterogeneity information based on the monitored electrical activity during delivery of His bundle pacing therapy at a one or more His bundle paced settings, wherein the His bundle therapy electrical heterogeneity information is representative of at least one of mechanical cardiac functionality and electrical cardiac functionality; and determining whether the one or more His bundle paced settings associated with the His bundle pacing therapy are acceptable based on the electrical heterogeneity information.

Embodiment 13

The method of embodiment 12, wherein the one or more His bundle paced settings includes at least one of a voltage, a pulse width, a location for the His bundle pacing therapy, a pacing polarity and vector, and a number of pacing electrodes used.

Embodiment 14

The method of any one of embodiments 12 to 13, further comprising assisting a user in selecting the one or more His bundle paced settings for the at least one implantable electrode to deliver the His bundle pacing therapy using a His bundle pacing therapy apparatus comprising at least one implantable electrode.

Embodiment 15

The method of any one of embodiments 12 to 14, further comprising positioning surface electrodes of the plurality of external electrodes in an array configured to be located proximate the skin of the torso of the patient.

Embodiment 16

The method of any one of embodiments 12 to 15, wherein the His bundle therapy electrical heterogeneity information comprises a therapy metric of electrical heterogeneity, wherein the determining whether the one or more His bundle paced settings for the His bundle pacing therapy are acceptable comprises:

determining whether intrinsic atrial ventricular (AV) conduction is not present; and in response to determining that the intrinsic AV conduction is not present, determining that the one or more His bundle paced settings for the His bundle pacing therapy are acceptable if the therapy metric of electrical heterogeneity is less than or equal to a threshold.

Embodiment 17

The method of any one of embodiments 12 to 16, wherein the determining whether the one or more His bundle paced settings for the His bundle pacing therapy are acceptable comprises:

determining whether intrinsic atrial ventricular (AV) conduction is present and synchronous;

in response to determining that the intrinsic AV conduction is present and synchronous, determining whether the one or more His bundle paced settings for the His bundle pacing therapy are acceptable based on at least one of:

comparing the His bundle therapy electrical heterogeneity information to a threshold; and comparing baseline electrical heterogeneity information generated from electrical activity monitored in the absence of His bundle pacing therapy to the His bundle therapy electrical heterogeneity information generated from electrical activity monitored during the His bundle pacing therapy.

Embodiment 18

The method of embodiment 17, wherein the baseline electrical heterogeneity information comprises a baseline metric of electrical heterogeneity and the His bundle therapy electrical heterogeneity information comprises a therapy metric of electrical heterogeneity, wherein comparing the baseline electrical heterogeneity information to the His bundle therapy electrical heterogeneity information comprises comparing a difference between the therapy metric of electrical heterogeneity and the baseline metric of electrical heterogeneity to a threshold.

Embodiment 19

The method of any one of embodiments 12 to 18, wherein the determining whether the one or more His bundle paced settings for the His bundle pacing therapy are acceptable comprises:

determining whether intrinsic atrial ventricular (AV) conduction is present;
in response to determining that the intrinsic AV conduction is present, determining whether intrinsic ventricular activation is asynchronous by comparing at least one of the metrics of electrical heterogeneity during the intrinsic AV conduction to a threshold;
in response to determining that the intrinsic AV conduction is present and asynchronous, determining whether the one or more His bundle paced settings for the His bundle pacing therapy are acceptable based on at least one of:
comparing the His bundle therapy electrical heterogeneity information to a threshold;
comparing baseline electrical heterogeneity information generated from electrical activity monitored in the absence of His bundle pacing therapy to the His bundle therapy electrical heterogeneity information.

Embodiment 20

The method of embodiment 19, wherein the baseline electrical heterogeneity information comprises a baseline metric of electrical heterogeneity and the His bundle therapy electrical heterogeneity information comprises a therapy metric of electrical heterogeneity,
wherein comparing the baseline electrical heterogeneity information to the His bundle therapy electrical heterogeneity information generated from the electrical activity monitored during the His bundle pacing therapy comprises comparing a difference between the therapy metric of electrical heterogeneity and the baseline metric of the baseline electrical heterogeneity information to a threshold.

Embodiment 21

The method of any one of embodiments 12 to 20, wherein the His bundle therapy electrical heterogeneity information comprises at least one therapy metric of electrical heterogeneity, wherein the at least one therapy metric of electrical heterogeneity comprises at least one of a standard deviation of activation times (SDAT), a mean left ventricular activation time (LVAT), and a mean right ventricular activation time (RVAT).

Embodiment 22

The method of embodiment 21, wherein the determining whether the one or more His bundle paced settings for the His bundle pacing therapy are acceptable comprises comparing the at least one therapy metric of electrical heterogeneity to a threshold.

Embodiment 23

A system comprising:
electrode apparatus comprising a plurality of external electrodes to monitor electrical activity from tissue of a patient; and
computing apparatus comprising processing circuitry and coupled to the electrode apparatus and configured to:
monitor electrical activity using the plurality of external electrodes during delivery of His bundle pacing therapy;
generate electrical heterogeneity information during delivery of His bundle pacing therapy;
determine whether a His bundle paced setting for the His bundle pacing therapy is acceptable based on the electrical heterogeneity information generated from the electrical activity using the His bundle paced setting; and
adjust the paced setting for the His bundle pacing therapy based on whether the His bundle pacing therapy is acceptable.

Embodiment 24

The system of embodiment 23, wherein the paced setting is adjusted in response to the His bundle paced setting being unacceptable.

Embodiment 25

The system of any one of embodiments 23 to 24, wherein the computing apparatus is further configured to determine whether the adjusted His bundle paced setting for the His bundle pacing therapy is acceptable based on the electrical heterogeneity information generated from the electrical activity using the plurality of external electrodes during delivery of His bundle pacing therapy using the adjusted His bundle paced setting.

Embodiment 26

The system of any one of embodiments 23 to 25, wherein the adjusted His bundle paced setting is determined to be acceptable in response to the His bundle pacing therapy correcting a bundle branch block (BBB).

What is claimed:
1. A system comprising:
electrode apparatus comprising a plurality of external electrodes to monitor electrical activity from tissue of a patient; and
computing apparatus comprising processing circuitry and coupled to the electrode apparatus and configured to:
monitor electrical activity using the plurality of external electrodes resulting in a plurality of cardiac signals;
generate His bundle electrical heterogeneity information based on the plurality of cardiac signals during delivery of His bundle pacing therapy at one or more His bundle paced settings, wherein the His bundle electrical heterogeneity information is representative of at least one of mechanical cardiac functionality and electrical cardiac functionality; and
determine whether one or more of the His bundle paced settings for the His bundle pacing therapy are acceptable based on the electrical heterogeneity information.

2. The system of claim 1, wherein the one or more His bundle paced settings comprise at least one of a voltage, a pulse width, a location for the His bundle pacing therapy, pacing polarity and vector, and number of pacing electrodes used.

3. The system of claim 1, wherein the system further comprises a His bundle pacing therapy apparatus comprising at least one implantable electrode, wherein the system is configured to assist a user in selecting an implant location for the at least one implantable electrode to deliver the His bundle pacing therapy.

4. The system of claim 1, wherein the plurality of external electrodes comprises surface electrodes positioned in an array configured to be located proximate the skin of a torso of the patient.

5. The system of claim 1, wherein the electrical heterogeneity information comprises a metric of electrical heterogeneity, wherein the determining whether the one or more of the His bundle paced settings for the His bundle pacing therapy are acceptable comprises:
- determining whether intrinsic atrial ventricular (AV) conduction is not present; and
- in response to determining that the intrinsic AV conduction is not present, determining that the one or more His bundle paced settings for the His bundle pacing therapy are acceptable if the metric of electrical heterogeneity is less than or equal to a threshold.

6. The system of claim 1, wherein the determining whether the one or more of the His bundle paced settings for the His bundle pacing therapy are acceptable comprises:
- determining whether intrinsic atrial ventricular (AV) conduction is present; and
- in response to determining that the intrinsic AV conduction is present, determining whether intrinsic ventricular activation is synchronous by comparing at least one of the metrics of electrical heterogeneity during the intrinsic AV conduction to a threshold;
- in response to determining that the intrinsic AV conduction is present and synchronous, determining whether the one or more His bundle paced settings for the His bundle pacing therapy are acceptable based on at least one of:
- comparing the His bundle pacing therapy electrical heterogeneity information to a threshold; and
- comparing baseline electrical heterogeneity information generated from electrical activity monitored in the absence of His bundle pacing therapy to the His bundle therapy electrical heterogeneity information generated from electrical activity monitored during the His bundle pacing therapy.

7. The system of claim 6, wherein each of the baseline and His bundle therapy electrical heterogeneity information comprises a metric of electrical heterogeneity,
- wherein comparing baseline electrical heterogeneity information to His bundle therapy electrical heterogeneity information generated from electrical activity monitored during His bundle pacing therapy comprises comparing a difference between the metric of electrical heterogeneity of the His bundle therapy electrical heterogeneity information and the metric of electrical heterogeneity of the baseline electrical heterogeneity information to a threshold.

8. The system of claim 1, wherein the determining whether the one or more of the His bundle paced settings for the His bundle pacing therapy are acceptable comprises:
- determining whether intrinsic atrial ventricular (AV) conduction is present;
- in response to determining that the intrinsic AV conduction is present, determining whether intrinsic ventricular activation is asynchronous by comparing at least one of the metrics of electrical heterogeneity during the intrinsic AV conduction to a threshold;
- in response to determining that the intrinsic AV conduction is present and asynchronous, determining whether the one or more His bundle paced settings for the His bundle pacing therapy are acceptable based on at least one of:
- comparing the electrical heterogeneity information to a threshold; and
- comparing baseline electrical heterogeneity information generated from electrical activity monitored in the absence of His bundle pacing therapy to His bundle therapy electrical heterogeneity information generated from electrical activity monitored during the His bundle pacing therapy.

9. The system of claim 8, wherein each of the baseline and the His bundle therapy electrical heterogeneity information comprises a metric of electrical heterogeneity,
- wherein comparing the baseline electrical heterogeneity information to the His bundle therapy electrical heterogeneity information generated from the electrical activity monitored during the His bundle pacing therapy comprises comparing a difference between the metric of electrical heterogeneity of the His bundle therapy electrical heterogeneity information and the metric of the baseline electrical heterogeneity information to a threshold.

10. The system of claim 1, wherein the electrical heterogeneity information comprises at least one metric of electrical heterogeneity, wherein the at least one metric of electrical heterogeneity comprises at least one of a standard deviation of activation times (SDAT), a mean left ventricular activation time (LVAT), and a mean right ventricular activation time (RVAT).

11. The system of claim 10, wherein the determining whether the one or more His bundle paced settings for the His bundle pacing therapy are acceptable comprises comparing the at least one metric of electrical heterogeneity to a threshold.

12. The system of claim 1, wherein generating His bundle electrical heterogeneity information based on the plurality of cardiac signals comprising:
- generating surrogate cardiac electrical activation times representative of depolarization of cardiac tissue that propagates through the torso of the patient; and
- determining the His bundle electrical heterogeneity information based on the surrogate cardiac electrical activation times.

13. A system comprising:
- electrode apparatus comprising a plurality of external electrodes to monitor electrical activity from tissue of a patient; and
- computing apparatus comprising processing circuitry and coupled to the electrode apparatus and configured to:
- monitor electrical activity using the plurality of external electrodes during delivery of His bundle pacing therapy resulting in a plurality of cardiac signals;
- generate electrical heterogeneity information based on the plurality of cardiac signals during delivery of His bundle pacing therapy;
- determine whether a His bundle paced setting for the His bundle pacing therapy is acceptable based on the electrical heterogeneity information generated from the plurality of cardiac signals using the His bundle paced setting; and
- adjust the paced setting for the His bundle pacing therapy based on whether the His bundle pacing therapy is acceptable.

14. The system of claim 13, wherein the paced setting is adjusted in response to the His bundle paced setting being unacceptable.

15. The system of claim 13, wherein the computing apparatus is further configured to determine whether the adjusted His bundle paced setting for the His bundle pacing therapy is acceptable based on the electrical heterogeneity information generated from the electrical activity using the plurality of external electrodes during delivery of His bundle pacing therapy using the adjusted His bundle paced setting.

16. The system of claim 13, wherein the adjusted His bundle paced setting is determined to be acceptable in response to the His bundle pacing therapy correcting a bundle branch block (BBB).

* * * * *